(12) United States Patent
McCool

(10) Patent No.: US 8,790,274 B2
(45) Date of Patent: Jul. 29, 2014

(54) NON-INVASIVE METHOD FOR MEASURING CHANGES IN BODY POSITION AND RESPIRATION

(76) Inventor: Franklin Dennis McCool, Bristol, RI (US)

( * ) Notice: Subject to any disclaimer, the term of this patent is extended or adjusted under 35 U.S.C. 154(b) by 271 days.

(21) Appl. No.: 13/345,082

(22) Filed: Jan. 6, 2012

(65) Prior Publication Data

US 2012/0179005 A1     Jul. 12, 2012

Related U.S. Application Data

(60) Provisional application No. 61/430,659, filed on Jan. 7, 2011.

(51) Int. Cl.
| | | |
|---|---|---|
| *A61B 5/08* | (2006.01) | |
| *A61B 5/11* | (2006.01) | |
| *A61B 5/113* | (2006.01) | |
| *A61B 5/05* | (2006.01) | |
| *A61B 5/00* | (2006.01) | |

(52) U.S. Cl.
CPC ........... *A61B 5/113* (2013.01); *A61B 2562/226* (2013.01); *A61B 5/05* (2013.01); *A61B 5/1116* (2013.01); *A61B 5/0806* (2013.01); *A61B 5/6823* (2013.01); *A61B 5/4818* (2013.01)
USPC ........................................................ 600/534

(58) Field of Classification Search
USPC .......................................... 600/301, 529, 534
See application file for complete search history.

(56) References Cited

U.S. PATENT DOCUMENTS

| | | | |
|---|---|---|---|
| 7,841,987 B2* | 11/2010 | Sotos et al. | 600/529 |
| 2005/0107722 A1* | 5/2005 | Ozaki et al. | 600/587 |
| 2006/0025827 A1* | 2/2006 | Hatlesad et al. | 607/17 |

OTHER PUBLICATIONS

Cantineau et al. Accuracy of respiratory inductive plethysmography during wakefulness and sleep in patients with obstructive sleep apnea. Chest 1992; 102:1145-1151.*
Robertson et al., "Comparison of two- and four-magnetometer methods of measuring ventilation" J.Appl. Phsiol. Respirat. Environ. Exercise Physiol. 49(3): pp. 355-362, 1980.
Smith et al., "Three degree of freedom description of movement of the human chest wall" The American Physiological Society, pp. 928-934,1986.
McCool et al., "Tidal Volume and Respiratory Timing Derived from a Portable Ventilation Monitor" Chest, Official publication of American College of Chest Physicians,pp. 684-692, 2002.
Konno et al., "Measurement of the separate volume changes of rib cage and abdomen during breathing" J. Appl. Physiol. 22(3): pp. 407-422, 1967.

(Continued)

*Primary Examiner* — Navin Natnithithadha
*Assistant Examiner* — Etsub Berhanu
(74) *Attorney, Agent, or Firm* — Gesmer Updegrove LLP

(57) ABSTRACT

A method and system of simultaneously monitoring body position and respiration of a subject are provided. The end-expiratory value of an axial dimension of a distance Xi between a first location and a second location is monitored for the subject orientation, and is then assigned a body position for the subject orientation during a calibration maneuver in which the subject is asked to assume various body positions. The transient voltage spikes in Xi voltage are measured to determine when the subject orientation changes. Following the subject orientation change, the stable end-expiratory voltage is determined to define a new body position. The new body position is outputted to a data output interface communicating with varied output devices.

14 Claims, 19 Drawing Sheets

(56) References Cited

OTHER PUBLICATIONS

McCool et al., "Rib cage distortion during voluntary and involuntary breathing acts" The American Physiological Society, pp. 1703-1712, 1985.

McCool et al., "Estimates of ventilation from body surface measurements in unrestrained subjects" The American Physiological Society, pp. 1114-1119, 1986.

Paek et al., "Breathing patterns during varied activities" The American Physiological Society, J. Appl. Physiol. 73(3): pp. 887-893, 1992.

Paek et al., "Postural effects on measurements of tidal volume from body surface displacements" The American Physiological Society, J. Appl. Physiol. 68(6): pp. 2482-2487, 1990.

Stagg et al., "Computer-aided measurement of breath volume and time components using magnetometers" The American Physiological Society, J. Appl. Physiol. 44(4): pp. 623-633, 1978.

Ballard et al., "Estimates of Ventilation fro, inductance Plethysmography in Sleeping Asthmatic Patients" Chest, Official publication of the American College of Chest Physicians, pp. 128-133, 1988.

Mead et al., "Pulmonary Ventilation Measured from Body Surface Movements" Science, vol. 156, No. 3780, pp. 1383-1384, 1967.

Wade, "Movements of the Thoracic Cage and Diaphragm in Respiration" J. Physiol. 124, pp. 193-212, 1954.

Whyte et al. "Accuracy of respiratory inductive plethysmograph in measuring tidal volume during sleep" The American Physiological Society, Physiol. 71(5):pp. 1866-1871, 1991.

Abu-Hijleh et al., "Tidal Volume and Respiratory Timing Derived form a Ventilation Monitor in 3 Different Sleep Positions" Am J Resp Crit Care Med. 163(5):A412 2001.

McCool et al., "Efficacy of a Portable Ventilation Monitor for Detecting Apneas and Hypopneas" Am J of Resp and Crit Care Med. 165(8):A408 2002.

* cited by examiner

Figure 12
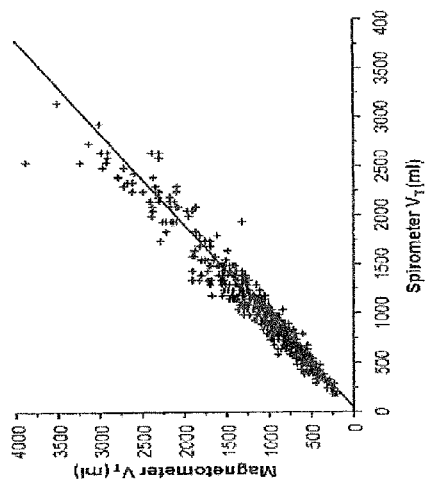
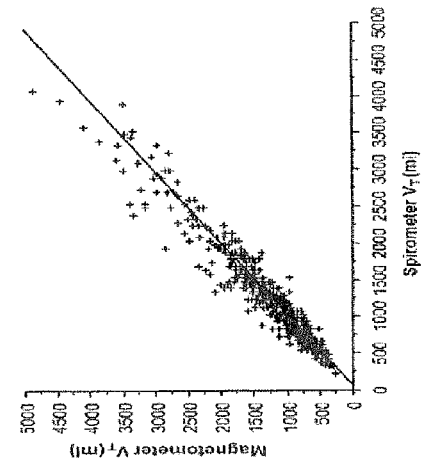

QUIET SLEEP

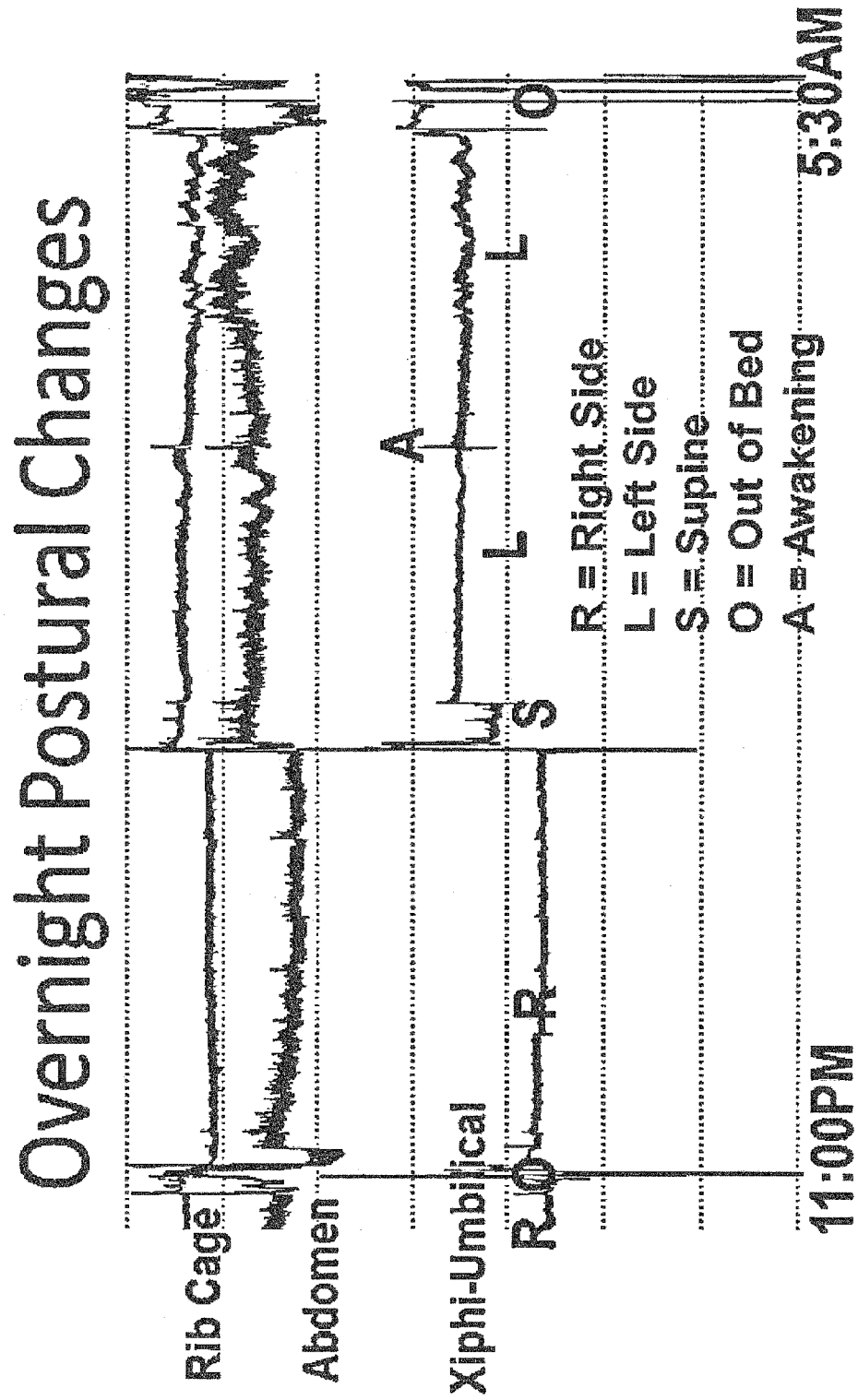

NON-INVASIVE METHOD FOR MEASURING CHANGES IN BODY POSITION AND RESPIRATION

PRIORITY INFORMATION

This application claims priority from provisional application Ser. No. 61/430,659 filed Jan. 7, 2011, which is incorporated herein by reference in its entirety.

BACKGROUND OF THE INVENTION

As is well known in the art, in medical diagnosis and treatment, it is often desirable to quantitatively measure over time changes in body position. This has conventionally been done by having an attendant record changes in posture.

As is well known in the art, in medical diagnosis and treatment, it is often desirable to quantitatively measure over time the respiratory air volume or pulmonary ventilation. This has conventionally been done by having the patient or subject breathe into a mouthpiece connected to a flow rate measuring device. Flow rate is then integrated to provide air volume change.

There are, however, several drawbacks and disadvantages associated with employing a mouthpiece. A mouthpiece is difficult to use for long term subject monitoring, especially for ill, sleeping, or anesthetized subjects. Further, it is uncomfortable for the subject, tends to restrict breathing, and is generally inconvenient for the physician or technician to use.

As is also well known in the art, there are qualitative respiration monitors available that do not require a mouthpiece. Illustrative are the systems disclosed in U.S. Pat. Nos. 3,831,586 and 4,033,332. Although the noted systems eliminate most of the disadvantages associated with a mouthpiece, the systems do not, in general, provide an accurate measurement of air volume. Further, the systems are typically only used to signal an attendant when a subject's breathing activity changes sharply or stops.

Another means for quantitatively measuring respiratory or lung volume is to measure the change in size of the rib cage and abdomen, as it is well known that lung volume is a function of these two parameters. A number of systems and devices have been employed to measure the change in size (i.e. Δ circumference) of the rib cage and abdomen, including mercury in rubber strain gauges, pneumobelts, magnetometers, and respiratory inductive plethysmograph (RIP) belts. These systems, in general, provide an accurate measurement of air volume when body position does not change.

In practice, respiratory magnetometers and RIP belts are primarily used to measure the change in size of the rib cage and abdomen. As is well known in the art, respiratory magnetometers consist of tuned pairs of electromagnetic coils or magnetometers; one coil being adapted to transmit a specific high frequency AC electromagnetic field (i.e. transducer) and the other coil (i.e. receiver) being adapted to receive the field. To measure the anteroposterior diameter of the rib cage, a first coil, e.g., transducer, is typically placed over the sternum at the level of the 4th intercostal space and the second coil (of the pair) is placed over the spine at the same level. To measure the anteroposterior diameter of the abdomen, a third coil is typically placed on the abdomen at the level of the umbilicus and a fourth coil (of the pair) is placed over the spine at the same level.

Over the operational range of distances, the output voltage is linearly related to the distance between a pair of coils; provided, the axes of the coils or magnetometers remain parallel to each other. As rotation of the axes can change the voltage, the transducer and receiver coils must be secured to the skin in a parallel fashion and rotation due to the motion of underlying soft tissue that must be minimized.

A potential limitation of the use of such coils or magnetometers is presented in environments that contain large metal structures or electric motors. Such devices produce extraneous electromagnetic fields and consequently affect the magnetometer voltage output.

Displacement (i.e. motion) of the rib cage can be directly assessed. Diaphragm displacement cannot be measured directly, but since the abdominal contents are essentially incompressible, caudal motion of the diaphragm relative to the pelvis and the volume it displaces is reflected by outward movement of the anterolateral abdominal wall.

The "two-degrees-of-freedom" model embraced by most in the field holds that the volume displacement of the respiratory system, i.e. tidal volume ($V_T$), is equal to the sum of the volume displacements of the rib cage and abdomen, i.e.

$$V_T = \alpha RC + \beta Ab \qquad \text{Eq. 1}$$

where:
RC and Ab represent linear displacements of the rib cage and abdomen, respectively; and $\alpha$ and $\beta$ represent volume-motion coefficients.

As is well known in the art, RC and Ab linear displacements are converted to RC and Ab volume displacements when multiplied by the $\alpha$ and $\beta$ volume-motion coefficients.

It is well established that the use of the noted "two-degrees-of-freedom" model can provide an estimate of $V_T$ that is within 10% accuracy of ventilation measured at the mouth; provided, the subject is confined to one body position.

Two different approaches primarily used for determining the necessary volume-motion coefficients of the rib cage and abdomen are the isovolume technique and the multiple linear regression technique. In the isovolume technique, the subject first performs an isovolume maneuver, shifting volume back and forth between the rib cage and abdominal compartments while holding the glottis closed, whereby there is no net volume change of the system. Since $V_T$ equals zero, Equation 1 can be modified as follows:

$$RC = (-\beta/\alpha) Ab \qquad \text{Eq. 2}$$

On a graph of rib cage and abdomen signals, the slope of the isovolume line is equal to the ratio $-\beta/\alpha$.

In practice, the gains of the rib cage and abdomen signals are often adjusted, whereby the slope of the isovolume line equals one. The rib cage and abdomen displacements are thus equal for any volume change. The two signals can then be directly summed to provide volume.

The isovolume method is based on the assumptions that displacements of the surfaces of the rib cage and abdomen are representatively sampled at the measured location, and are similar during isovolume efforts and spontaneous breathing. Since volume-motion coefficients change with posture, the isovolume calibration must be repeated in each body position.

Computer-assisted regression techniques, such as multiple linear regression, are used to determine volume-motion coefficients by solving a matrix of multiple simultaneous equations of changes in chest wall dimensions and lung volume. An advantage of these techniques is that no special calibration maneuver is required to generate volume-motion coefficients.

A limitation of any approach that uses chest wall motion to assess ventilation is, however, that the overall volume change of the chest wall being measured includes not only changes in lung volume, but also blood volume shifts into and out of the thoracoabdominal cavity. This can occur when the respiratory system is subjected to large pressure changes, or with changes in posture (e.g. between supine and upright position).

Another limitation is related to distortion that can occur within the rib cage or abdomen (e.g. between the upper and lower rib cage or between the lower transverse and AP rib cage).

It is proposed to use the following "three-degrees-of-freedom" model to determine tidal volume, i.e.

$$V_T = \alpha RC + \beta Ab + \gamma Xi \qquad \text{Eq. 3}$$

where:
RC and Ab represent linear displacements of the rib cage and abdomen, respectively; Xi represents the Δ distance between the xiphoid and the pubic symphysis; and α, β and γ represent volume-motion coefficients for RC, Ab and Xi.

There are, however, similarly several drawbacks and disadvantages associated with the 'three-degrees-of-freedom" model. A major drawback is that the 'three-degrees-of-freedom" model reflected in Eq. 3 above is still limited in accuracy to about 15% of actual ventilation in individuals who are doing freely moving postural tasks, such as bending, sitting or standing, due to spinal flexion.

It would thus be desirable to provide an improved method and associated system for determining tidal volume (or pulmonary ventilation) that substantially reduces or eliminates the drawbacks and disadvantages associated with conventional methods and systems that are employed to determine pulmonary ventilation.

As is well known in the art, assessing changes in body position is an integral component of the diagnosis and treatment of sleep apnea. It is important to ascertain body position during sleep as sleep disordered breathing may be position dependent.

Sleep apnea is a disorder that affects 5-10% of the population. The supine sleep position often favors the development of apneas and hypopneas. Body position is often documented by a technician in a sleep lab. Drawbacks to performing overnight polysomnography in a sleep lab include sleep fragmentation brought about by an individual sleeping in a foreign setting outside the home and the need for a technician to attend the procedure and document changes in body position.

It is important to have non-invasive methods to ascertain body position which do not require the presence of an attendant. This would allow for remote assessment of body position.

Apneas and hypopneas are detected by analyzing breathing pattern during sleep. Apneas are defined as a cessation of airflow for greater than 10 seconds and a hypopnea is defined as a greater than 50% reduction in airflow lasting at least 10 seconds and associated with oxyhemoglobin desaturation of 3% or greater. Currently, numerous methods are utilized to determine apneas and hypopneas including measurement of motion of the rib cage and abdomen. These methods do not accurately measure the amount of air inhaled or exhaled (tidal volume; $V_T$). This failure in methodology, which is common to all commercially available polysomnography systems, makes detecting hypopneas subjective and variable among scorers.

SUMMARY OF THE INVENTION

According to one aspect of the invention, there is provided a method of simultaneously monitoring body position and respiration of a subject. The method includes monitoring a subject orientation, monitoring an end-expiratory value of an axial dimension of a distance Xi between a first location and a second location for the subject orientation, and assigning a body position for the end-expiratory value for the subject orientation during a calibration maneuver in which the subject is asked to assume varied body positions. Additionally, the method includes determining when the subject orientation changes by measuring transient voltage spikes, determining the end-expiratory value that is stable following the subject orientation change, and defining a new body position. Further, the method includes providing the new body position data to a data output interface communicating with varied output devices.

According to another aspect of the invention, there is provided a pulmonary ventilation system of simultaneously monitoring body position and respiration of a subject. The pulmonary ventilation system includes means for monitoring a subject orientation, so as to allow monitoring of an end-expiratory value of an axial dimension of a distance Xi between a first location and a second location for the subject orientation, and means for assigning a body position for the end-expiratory value for the subject orientation during a calibration maneuver in which the subject is asked to assume varied body positions. Transient voltage spikes are used to signal a change in subject orientation. Additionally, the pulmonary ventilation system includes means for determining the end-expiratory value that is stable following the subject orientation change and defining a new body position, where the new body position is outputted to a data output interface communicating with varied output devices.

BRIEF DESCRIPTION OF THE DRAWINGS

FIG. 12 demonstrates the relationship between magnetometer and pneumotach derived tidal volumes for non-obese and obese awake subjects;

FIG. 18 is an exemplar recording of the simultaneous measure of body position and breathing pattern in a sleeping individual during an overnight study.

DETAILED DESCRIPTION OF THE INVENTION

Figure 1A:
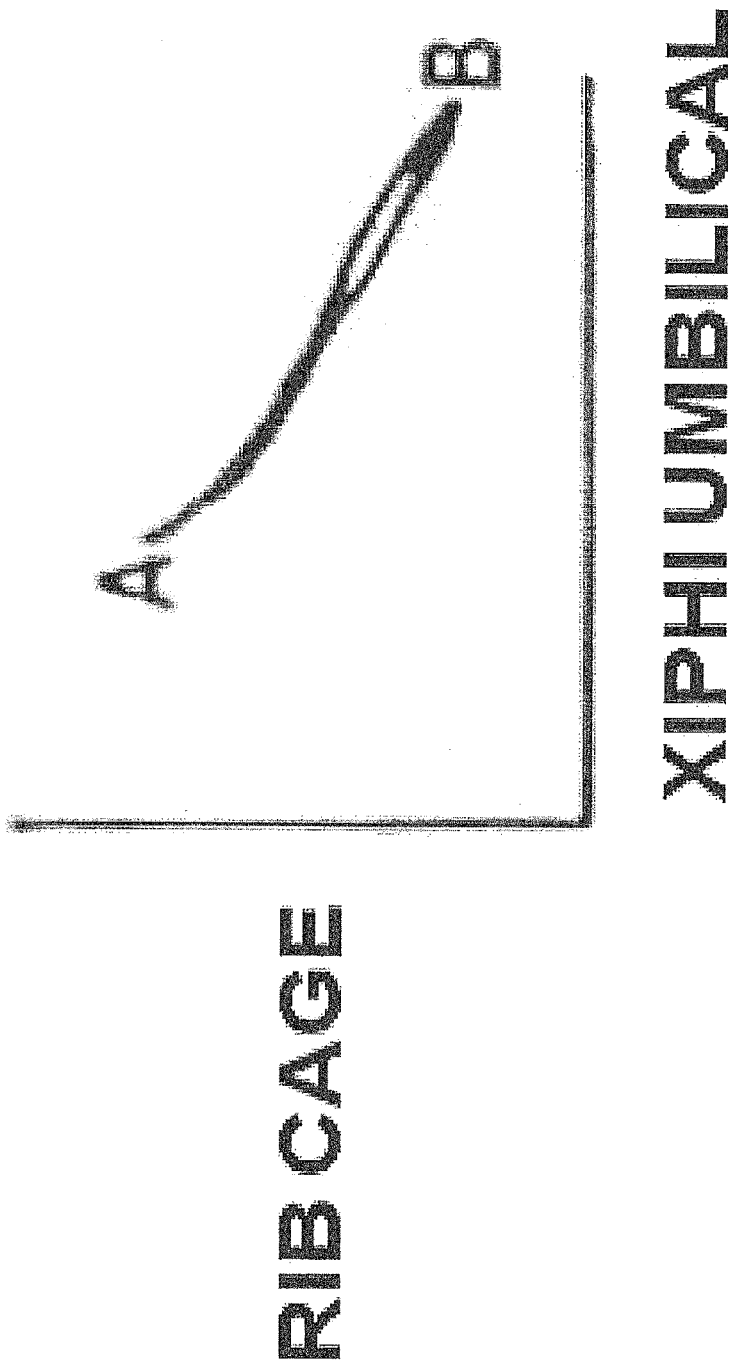
FIG. 1A is a graphical representation of the "displacement" error due to changes in spinal attitude.

It is to be understood that the terminology used herein is for the purpose of describing particular embodiments of the invention only, and is not intended to be limiting.

Unless defined otherwise, all technical and scientific terms used herein have the same meaning as commonly understood by one having ordinary skill in the art to which the invention pertains.

DEFINITIONS

The terms "ventilation parameter" and "ventilation characteristic", as used herein, mean and include, a characteristic associated with the respiratory system and functioning thereof, including, without limitation, total pulmonary ventilation, inspiration volume ($V_I$), expiration volume ($V_E$), breathing frequency, inspiratory breathing time and expiratory breathing time.

The term "apnea", as used herein, means and includes the temporary cessation of respiration or a reduction in the respiration rate.

The term "hypopnea", as used herein, means and includes abnormally shallow breathing or a slow respiratory rate.

The terms "respiratory system disorder", "respiratory disorder" and "adverse respiratory event", as used herein, mean and include any dysfunction of the respiratory system that impedes the normal respiration or ventilation process, including, without limitation, an apnea and/or hypopnea.

As will be appreciated by one having ordinary skill in the art, the present invention is directed to noninvasive methods and associated systems for determining pulmonary ventilation that substantially reduce or eliminate the drawbacks and disadvantages associated with conventional methods and systems for determining pulmonary ventilation.

As discussed in detail herein, one major advantage of the present invention is that the noninvasive methods and associated systems for determining body position and pulmonary ventilation can be readily employed to monitor breathing in different positions while awake and during sleep, and accurately detect respiratory events, such sleep apnea and hypopnea, during sleep.

As is known in the art, sleep apnea is generally defined as a temporary cessation of respiration during sleep. Obstructive sleep apnea is the recurrent occlusion of the upper airways of the respiratory system during sleep. Central sleep apnea occurs when the brain fails to send the appropriate signals to the breathing muscles to initiate respirations during sleep. Those afflicted with sleep apnea experience sleep fragmentation and complete cessation of respiration (or ventilation) during sleep with potentially severe degrees of oxyhemoglobin desaturation.

Sleep hypopnea is generally defined as abnormally shallow breathing or a slow respiratory rate. Hypopnea differs from apnea in that there remains some air flow.

Respiratory inductive plythysmograph (RIP) belts consist of two loops of wire that are coiled and sewed into an elastic belt. To measure changes in cross-sectional areas of the rib cage and abdomen, one belt is secured around the mid-thorax and a second belt is placed around the mid-abdomen.

The voltage change from the belts is generally linearly related to changes in the enclosed cross-sectional area. When the RIP belts are operated in the DC-coupled mode, they can detect shifts in chest wall dimensions, e.g. a change of FRC. However, the AC-coupled mode is typically preferred for tidal volume measurements.

For quantitative measurements, RIP uses a "two-degrees-of-freedom" model to assess changes in perimeters (i.e. cross-sectional area) of the rib cage and abdomen. Since the first rib and adjacent structures of the neck are relatively immobile, the movable components of the thoracic cavity are taken to be the anterior and lateral walls of the rib cage and the abdomen. Changes in volume of the thoracic cavity will then be reflected by displacements of the rib cage and abdomen.

Monitoring breathing during sleep is the cornerstone to the diagnosis and management of various sleep disorders. The respiratory inductive plythysmograph (RIP) is the most widely used technology in the diagnosis of sleep disorders. As indicated, RIP uses a "two-degrees-of-freedom" model to derive tidal volume ($V_T$) from changes in the circumference (i.e. cross-sectional area) of the rib cage and abdomen.

As is well known in the art, there is a poor correlation between $V_T$ measured by a pneumotachograph and that measured by RIP during sleep. The inaccuracies in the RIP derived $V_T$ have been attributed to slippage of the RIP belts; a factor that would alter RIP calibration, and to changes in body position during sleep.

As will be appreciated by one having skill in the art, as a subject bends forward, the abdomen contents displace the diaphragm cephalad and this, in turn, expands the rib cage. It has been found that the overestimation of volume due to this "displacement error' can be as great as 40-50% of the vital capacity. Similar inaccuracies with RIP have been noted during sleep in asthmatic subjects with nocturnal bronchospasm and paradoxical chest wall motion.

As discussed in detail above, the accuracy of "two-degrees-of-freedom" model is limited by virtue of changes in spinal flexion that can accompany changes in posture. Indeed, it has been found that $V_T$ can be over or under-estimated by as much as 50% of the vital capacity with spinal flexion and extension.

There are two major causes that contribute to the change in body position induced "two-degrees-of-freedom" model error(s) and, hence, limitation. A first contributing cause of the error is due to the substantial displacement of the summed rib cage and abdomen signals that occurs with isovolume spinal flexion and extension or pelvic rotation.

These shifts are a consequence of conservation of volume. As one of the thoracoabdominal boundaries is pushed in, another must be pushed out.

The second contributing cause of the error is due to posturally-induced changes in volume-motion coefficients. With isovolume spinal flexion, the rib cage comes down with respect to the pelvis and the axial dimension of the anterior abdominal wall becomes smaller. Therefore, less abdominal cavity is bordered by the anterior abdominal wall.

With a smaller anterior abdominal wall surface to displace, a given volume displacement of the abdominal compartment would be accompanied by a greater outward displacement of the anterior abdominal wall. The abdominal volume-motion coefficient would accordingly be reduced.

It has, however, been found that the addition of a measure of the axial motion of the chest wall, e.g., Δ distance between the xiphoid and the pubic symphysis (Xi), provides a third degree of freedom, which, when employed to determine $V_T$ can reduce the error associated with the "two-degrees-of-freedom" model.

Although a "three-degrees-of-freedom" model can reduce the error associated with the "two-degrees-of-freedom" model, the "three-degrees-of-freedom" model is still limited in accuracy to about 15% of actual ventilation in individuals who are doing freely moving postural tasks, such as bending, lifting, sitting or standing, due to spinal flexion.

As indicated above, the most pronounced effect of spinal flexion is on the abdominal volume-motion coefficient (β). With bending, β decreases as the xiphi-umbilical distance decreases.

Eq. 3 has accordingly been modified as follows to incorporate the noted dependency:

$$V_T = \alpha(\Delta RC) + (\beta_u + \epsilon Xi) \times (\Delta Ab) + \gamma(\Delta Xi) \quad \text{Eq. 4}$$

where:
ΔRC represents the linear displacement of the rib cage;
ΔAb represents the linear displacement of the abdomen;
ΔXi represents the change in the xiphi-umbilical distance from an upright position;
α represents a rib cage volume-motion coefficient;
β represents an abdominal volume-motion coefficient;
$\beta_u$ represents the value of the abdominal volume-motion coefficient (β) in the upright position;
ε represents the linear slope of the relationship of β as a function of the xiphi-umbilical distance Xi;
$(B_u + \epsilon Xi)$ represents the corrected abdominal volume-motion coefficient; and
γ represents a xiphi-umbilical volume-motion coefficient.

Equation 4 represents a "three-degrees-of-freedom" model, which now reflects the dependence of β on the xiphi-umbilical distance.

According to the invention, tidal volume ($V_T$) can also be determined as a function of changes in the anteroposterior dimensions of the rib cage and abdomen, as well as the axial displacement of the chest wall, i.e.

$$V_T = \alpha(\Delta RC) + \beta(\Delta Ab) + \gamma(\Delta Xi) \quad \text{Eq. 5}$$

where:
ΔRC represents the linear displacement of the rib cage;
ΔAb represents the linear displacement of the abdomen;
ΔXi represents axial displacement of the chest wall;
α represents a rib cage volume-motion coefficient;
β represents an abdominal volume-motion coefficient; and
γ represents a chest wall volume-motion coefficient.

According to the invention, the axial displacement of the chest wall can be determined from various reference points.

Thus, in one embodiment of the invention, the xiphi-umbilical distance is measured to determine ΔXi. γ would thus represent a xiphi-umbilical volume-motion coefficient.

In a preferred embodiment of the invention, the sternal-umbilical distance is measured to determine ΔXi. γ would thus represent a sternal-umbilical volume-motion coefficient.

In one embodiment of the invention, the values of volume-motion coefficients α, β and γ are determined for three positions or orientations, i.e. supine, right and left lateral decubitus positions, by multiple linear regressions, as set forth in Stagg, et al., "Computer-aided Measurement of Breath Volume and Time Components Using Magnetometers", J. Appl. Physiol., vol. 44, pp. 623-633 (1978); which is expressly incorporated by reference herein. $V_T$ is then calculated after applying the noted volume-motion coefficients to the signals obtained in the same body position.

In one embodiment of the invention, the values of coefficients α, β and γ are determined during a plurality of motions or activities by multiple linear regressions.

The term "volume-motion coefficient", as used herein, thus means both coefficients representing body positions or orientations and motions of a subject.

As will readily be appreciated by one having ordinary skill in the art, the "three-degrees-of-freedom" models of the invention substantially reduce $V_T$ measurement errors associated with conventional two-degrees and three-degrees of freedom models resulting from changes in posture. Indeed, as set forth below, $V_T$, inspiration time ($T_I$), expiration time ($T_E$), inspiration flow ($V_I$), and expiration flow ($V_E$) can be accurately measured in various postures while awake and during sleep using the "three-degrees-of-freedom" models of the invention.

As discussed in detail below, the "three-degrees-of-freedom" models of the invention can also be readily employed to detect adverse respiration or ventilation events, such as apneas or hypopneas.

As indicated above, with bending, the xiphi-umbilical distance decreases. This feature allows one to employ the Xi signal as a monitor of posture and eliminate the need for an attendant.

Several embodiments of pulmonary ventilation systems of the invention will now be described in detail. It is, however, understood that the invention is not limited to the system embodiments described herein. Indeed, as will be appreciated by one having ordinary skill in the art, systems and associated circuits similar or equivalent to the described systems can also be employed within the scope of the present invention.

In general, the ventilation systems of the invention include means for storing an empirical relationship that is designed and adapted to determine at least one ventilation parameter as a function of a plurality of anatomical measurements and volume-motion coefficients, means for acquiring the anatomical measurements, means for determining the plurality of motion coefficients, and processing means for determining the ventilation parameter based on the acquired anatomical measurements and determined plurality of volume-motion coefficients.

In a preferred embodiment, the ventilation system further includes means for acquiring base-line ventilation characteristics and means for correlating the base-line ventilation characteristics to the ventilation parameter determined with the empirical relationship.

The ventilation systems of the invention are also preferably implemented in a compact, light-weight configuration that can be easily attached to or carried by, e.g. carrier vest, an individual being monitored.

Referring now to FIG. 1A, there is shown one embodiment of a graphical representation of the sources of error due to changes in the spinal attitude of the outward displacement of the rib cage associated with spinal flexion (displacement error).

Figure 1B:
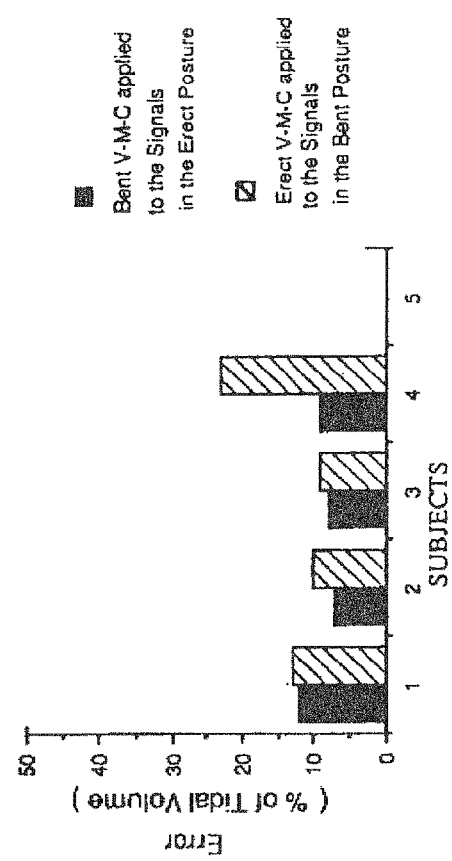
FIG. 1B is a graphical representation of the "coefficient" error due to changes in the spinal attitude.

Referring now to FIG. 1B, there is shown one embodiment of a graphical representation of the sources of error due to the changes in the spinal attitude of the alteration of volume-motion coefficients (coefficient error). Misapplication of volume-motion coefficients determined in one body position to another leads to erroneous calculation of tidal volume.

Figure 2:
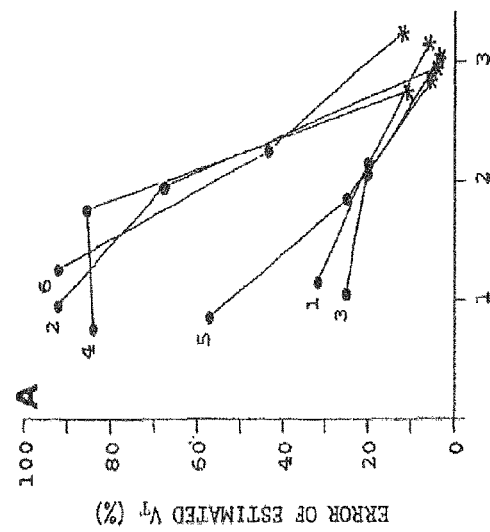
FIG. 2 is a graphical illustration of the percent error incurred during a maneuver that incorporates changes in spinal attitude.

Referring now to FIG. 2, there is shown one embodiment of a graphical illustration of the percent error incurred during a maneuver that incorporates changes in spinal attitude. The 3 degrees of freedom model (3) is more accurate than 1 or 2 degrees of freedom models (1 and 2). It can be seen that the use of a "three-degrees-of-freedom" model incorporating the third independent variable, i.e. the Δ distance between the xiphoid and the pubic symphysis ("Xi"), enhances the accuracy with which volume is estimated from body surface motion in those maneuvers that incorporate changes in spinal attitude.

Figure 3:
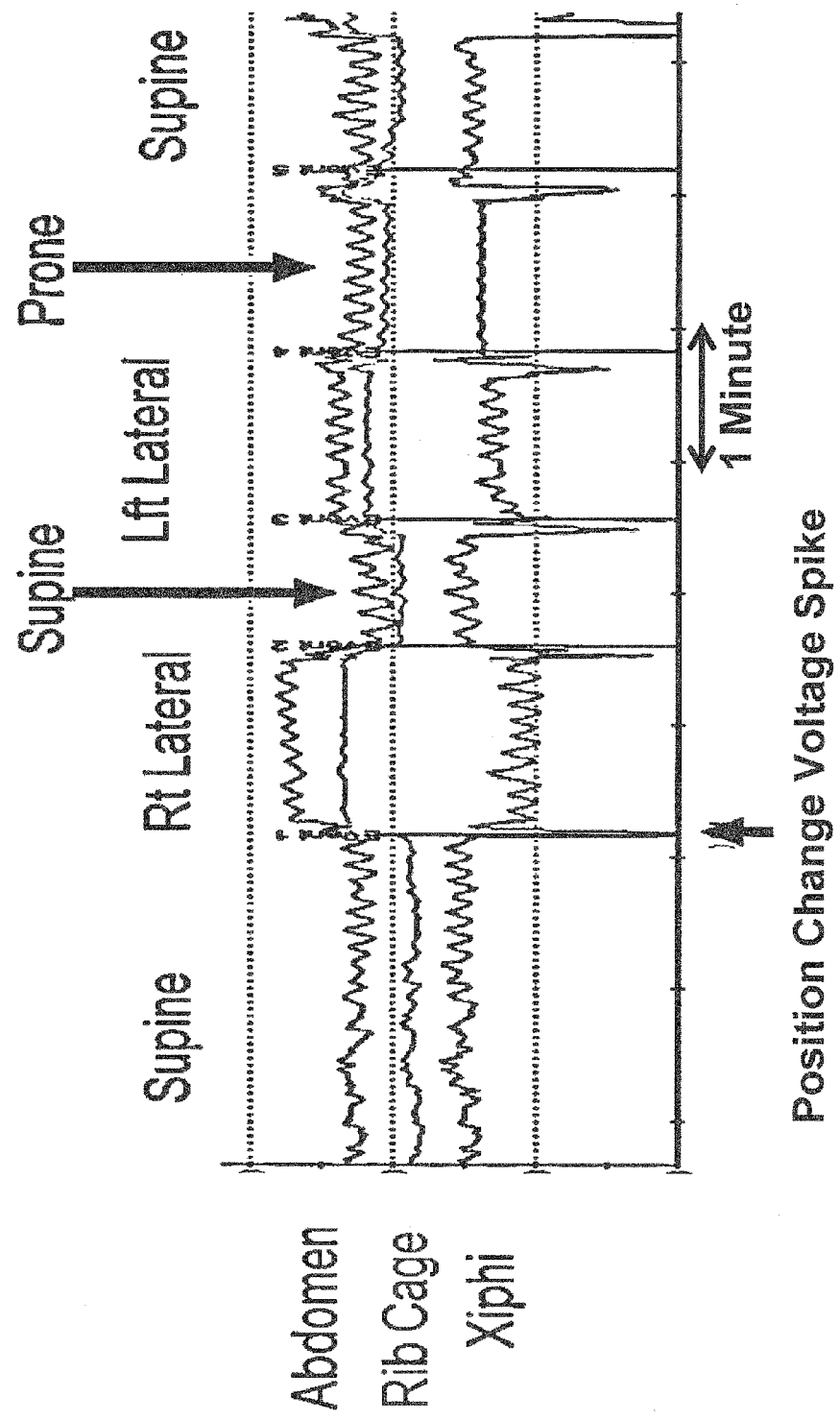
FIG. 3 is a graphical illustration of the position induced voltage spikes which herald a change in body position.

Referring now to FIG. 3, there is shown one embodiment of a graphical illustration of the position-induced voltage spikes which herald a change in body position. There is a transient spike in Xi voltage which heralds a change in body position. The new body position is associated with a new end-expiratory baseline (best seen in the Xi channel). Following the spike in Xi, there is a shift in end-expiratory voltage associated with the new body position. This feature allows for application of posture-specific volume-motion coefficients and provides the bases of a servomechanism for positive airway pressure (PAP) devices and mechanical ventilators.

Treatment of sleep apnea may be position-dependent. Application of positive airway pressure (PAP) via a nasal interface or full face mask is the most common method used to treat sleep apnea. The level of PAP required to treat an individual with sleep apnea may be greater in the supine position than in other sleep positions.

Current PAP devices that automatically adjust pressure when there is a position-dependent change in PAP requirements are limited in efficacy. PAP adjustments are accomplished by sensing changes in airways resistance or the presence of snoring. Drawbacks of this method include miscalculating airways resistance or improperly analyzing sound generated by snoring. In addition, individuals who have undergone surgical treatment of sleep apnea (surgery to remove soft tissue in the throat) may not generate sound in the frequencies typical for snoring. These limitations can be circumvented by developing an auto-titrating PAP device which uses magnetometry to sense changes in body position during sleep.

Figure 4:
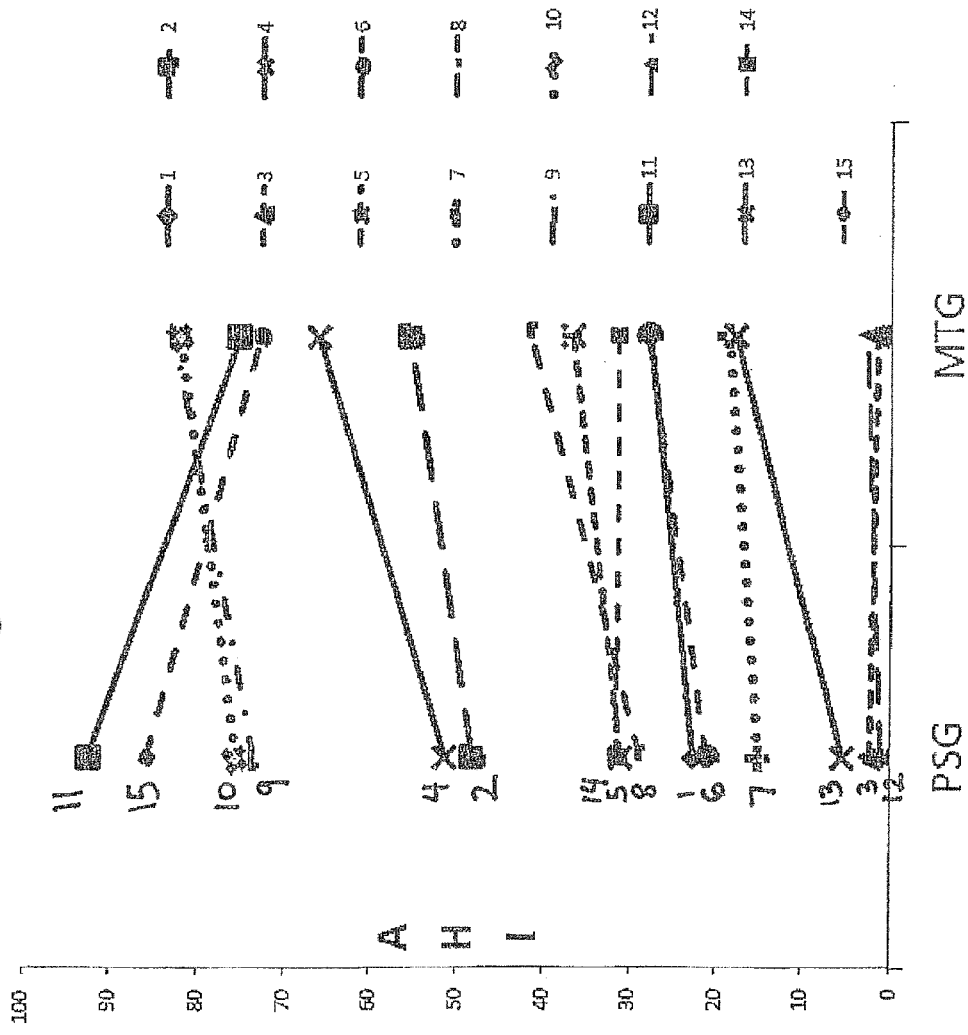
FIG. 4 is a graphical illustration of apnea and hypopnea indices for a plurality of monitored subjects, according to the invention.

Referring now to FIG. 4, there is shown one embodiment of a graphical illustration of apnea and hypopnea indices for a plurality of monitored subjects, according to the invention.

Figure 5:
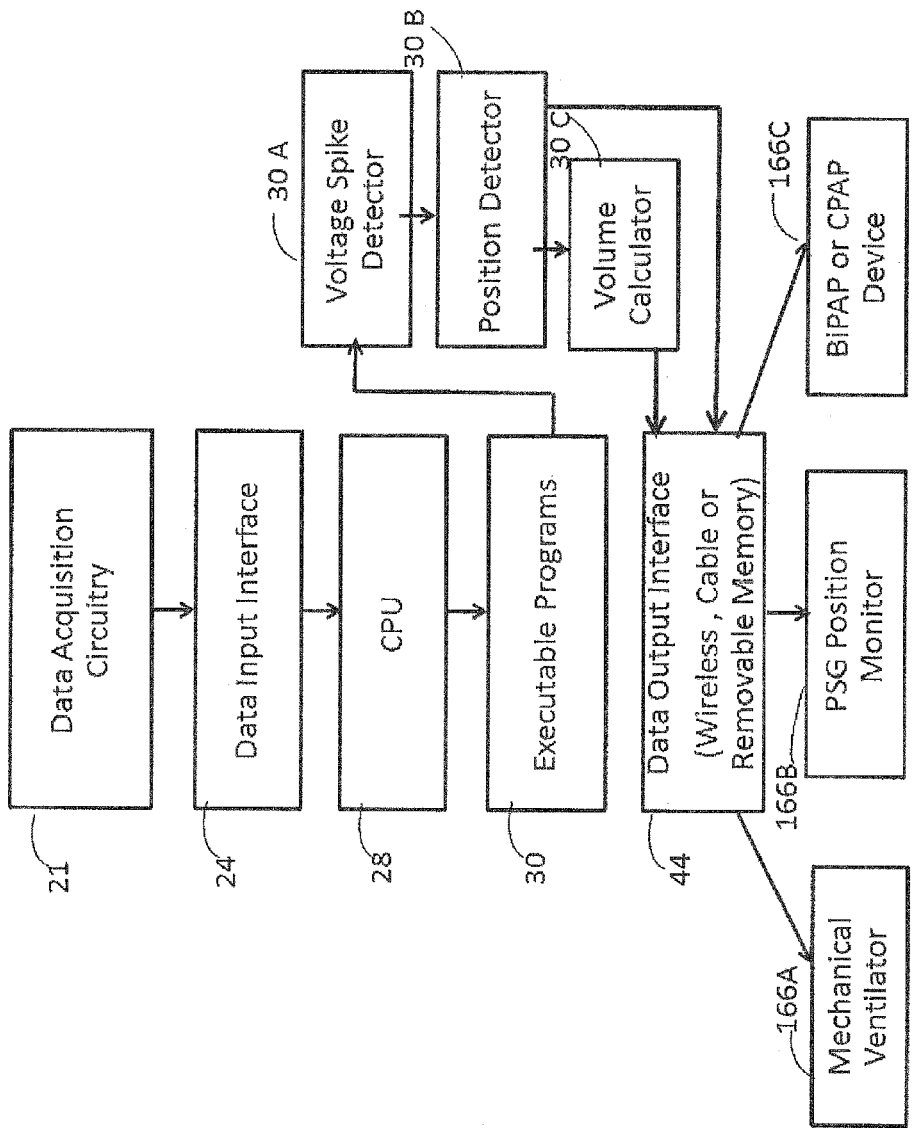
FIG. 5 is a block diagram schematic illustrating the sequence of signal processing in one embodiment of the invention.

Referring now to FIG. 5, there is shown one embodiment of a block diagram illustrating the sequence of signal processing. A data input interface 24 processes the signals from a data acquisition circuitry 21 and relays this data to a CPU 28 which includes a number of executable programs 30. A voltage spike detector 30A detects abrupt "spikes" in voltage and heralds a change in posture. Once a voltage spike is detected, a position detector 30B determines the bias end-expiratory voltage and assigns a unique body position to the new stable end-expiratory voltage. The new body position data is sent to a data output interface 44 which relays the new body position data to varied output devices such as a body position monitor used for polysomnography 166B, a PAP device used to treat sleep apnea 166C, or other devices which need to be adjusted when body position changes. Alternatively, the data from the body position detector 30B can be relayed to embodied program within a volume calculator 30C which is then inputted to a three degrees of freedom model which uses position specific volume motion coefficients to calculate tidal volume, respiratory timing, and changes in end-expiratory lung volume. The breathing pattern data is sent to a data output interface 44, which can communicate with varied respiratory monitors or mechanical ventilators 166A.

Figure 6:
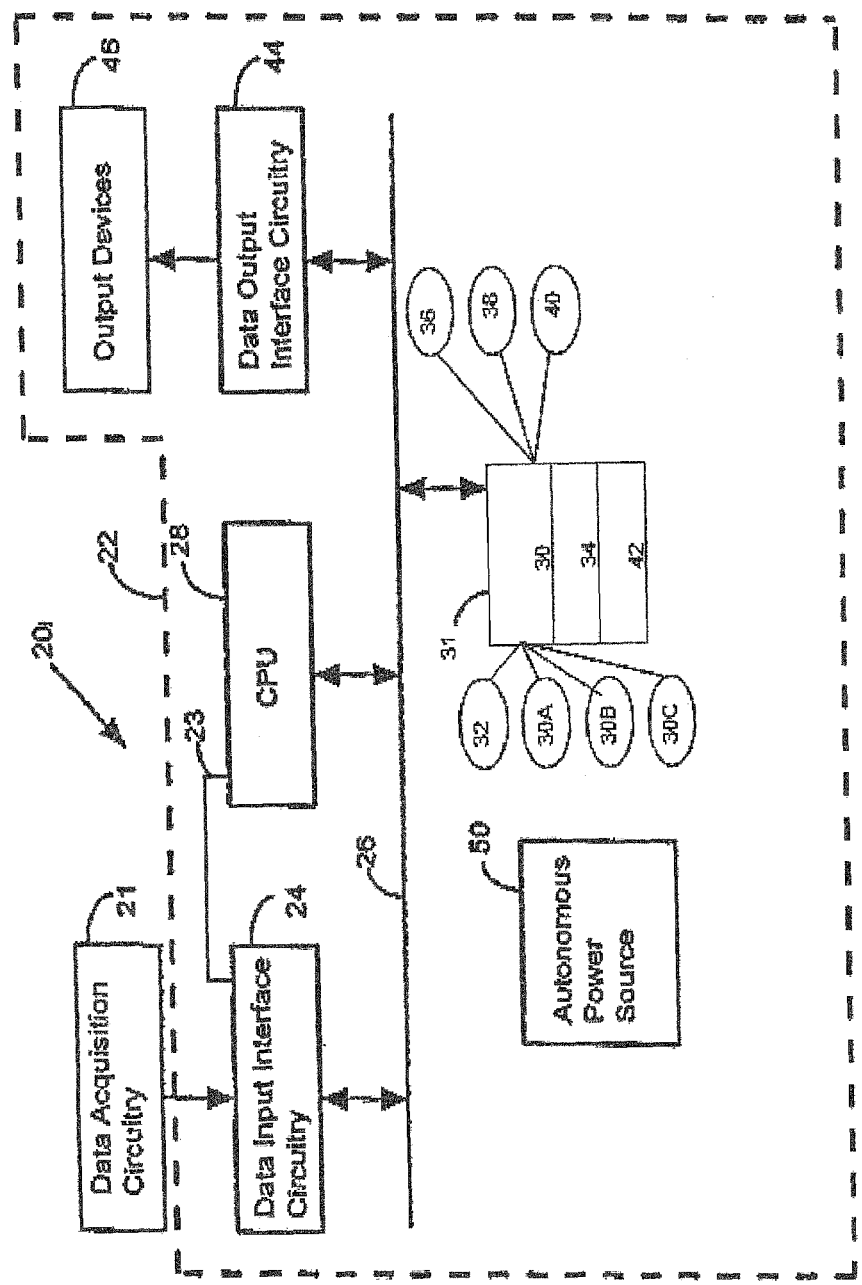
FIG. 6 is a schematic illustration of one embodiment of a pulmonary ventilation system of the invention.

Referring now to FIG. 6, there is shown one embodiment of a pulmonary ventilation system 20 of the invention. As illustrated in FIG. 6, the system 20 preferably includes data acquisition circuitry 21 and data processing circuitry 22.

The system 20 also includes a power source 50, such as a battery. In one embodiment of the invention, the system 20 is operable on 100 mA current from a +/−8.0V to +/−12.-V power source 50.

Figure 7:
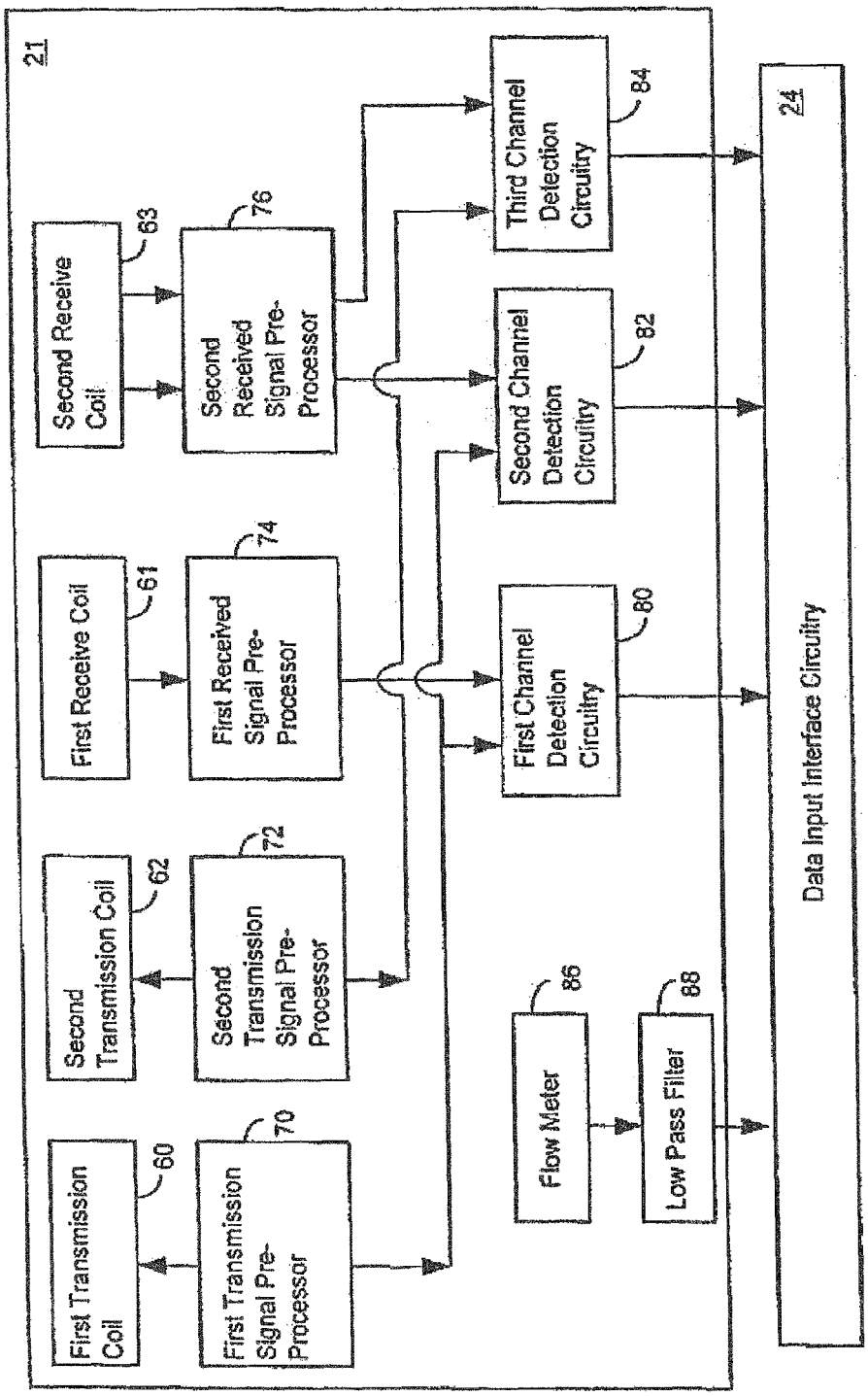
FIG. 7 is a schematic illustration of one embodiment of a pulmonary ventilation system data acquisition circuitry of the invention.

According to the invention, the data acquisition circuitry 21 includes data acquisition means, i.e. means for measuring (or sensing) changes in the anteroposterior diameters of the rib cage and abdomen, and axial displacement of the chest wall. In one embodiment of the invention, which is illustrated in FIG. 7 and discussed in detail below, the data acquisition means comprises paired electromagnetic coils 60-63.

It is, however, understood that the invention is not limited to the use of electromagnetic coils to measure changes in the anteroposterior diameters of the rib cage and abdomen, and axial displacement of the chest wall. Indeed, various additional means and devices that can be readily adapted to measure the noted anatomical parameters can be employed within the scope of the invention. Such means and devices include, without limitation, Hall effect sensors and electronic compass sensors.

Referring back to FIG. 6, in the illustrated embodiment, the data processing circuitry 22 includes data input interface circuitry 24, which is adapted to receive data from the data acquisition circuitry 21. According to the invention, the data input interface circuitry 24 facilitates data communication by and between the data acquisition circuitry 21 and the data processing circuitry 22.

In the illustrated embodiment, the data input circuitry 24 is in communication with (i.e. operatively connected to) system buses 23, 26, and transmits (or directs) signals thereto. The central processing unit (CPU) 28 is also preferably operatively connected to buses 23, 26.

As further illustrated in FIG. 6, bus 26 is in communication with memory 31, which includes at least one, more preferably, a plurality of executable programs 30. In one embodiment of the invention, the executable programs 30 include a calibration program (or routine) 32, a voltage spike detector 30A, a body position detector 30B, a volume calculator 30C, a signal processing or element analysis program 36, a ventilation parameter program 38, and an output program 40.

According to the invention, the central processing unit 28 executes selective programs 30 stored in the memory 31. The data provided by the programs, e.g. accumulated pulmonary ventilation data 42, and derived volume-motion coefficients are also preferably stored in the memory 31.

In some embodiments of the invention, the calibration program 32 comprises a routine for determining volume-motion coefficients in selective body positions and/or motions and calibrating the data acquisition circuitry 21. In a preferred embodiment, calibration of the data acquisition circuitry 21 is performed in a single step.

In some embodiments of the invention, the calibration program 32 is also adapted to "automatically" select derived volume-motion coefficients, i.e. a volume-motion coefficient data set, reflecting a specific body position (or posture) or activity to calibrate the data acquisition circuitry 21 when a subject or patient is in the noted body position or performing the activity.

According to the invention, the central processing unit 28 executes selective programs 30 which use the Xi signal to detect a transition to a new body position by a voltage spike detector 30A and to determine the specific body position by a position detector 30B. It then applies position-specific volume-motion coefficients stored in the memory 31 to calculate tidal volume for the specific body position.

The central processing unit 28 then executes a program within the position detector 30B coupled to a positive airway pressure device 166C through output program 40. The positive airway pressure device 166C is then adjusted to the appropriate pressure for treatment of position-dependent obstructive sleep apnea.

The element analysis program 36 is designed and adapted to perform element analyses on acquired signals (representing acquired data) to reduce any extraneous noise in the signals. In one embodiment of the invention, the element analyses include at least one Fourier analysis. The Fourier analysis, when combined with band pass filtering in the software, facilitates use of the system 20 in ambulatory activities.

In a preferred embodiment, the ventilation parameter program 38 employs at least one of the "three-degrees-of-freedom" models of the invention to determine at least one ventilation parameter, e.g., total pulmonary ventilation.

The output program 40 is designed and adapted to facilitate the visual display of acquired data, which can be displayed on an output device 46, e.g. a liquid crystal display, or, as discussed below, an external output device. As illustrated in FIG. 6, in the noted embodiment, the output device 46 is in communication and, hence, interacts with the CPU 28 through data output interface circuitry 44.

According to the invention, the data output interface circuitry 44 can be adapted to interact with external output devices, such as a personal computer, a printer, a monitor, a mechanical ventilator 166A, a polysomnography system 166B, a positive airway pressure device 166C used to treat sleep apnea, and the like. Communication by and between the data output interface circuitry 44 and external device(s) can be achieved via wired connections there between and/or wireless transmission.

As illustrated in FIG. 6, the memory 31 preferably includes at least one, preferably, a plurality of digital band pass filters 34. According to the invention, the digital band pass filters 34 are designed and employed to eliminate extraneous noise or artifacts resulting from soft tissue motion.

Referring now to FIG. 7, there is shown one embodiment of the data acquisition circuitry 21 of the invention. As illustrated in FIG. 7, the data acquisition circuitry 21 preferably includes a first transmission coil 60, a second transmission coil 62, a first receive coil 61 and a second receive coil 63.

In a preferred embodiment of the invention, at least one of the two receive coils 61, 63 is adapted to receive transmissions (or process signals) from each of the transmission coils 60, 62, i.e. dual functionality.

Accordingly, in one embodiment of the invention, the first transmission coil 60 comprises a first frequency (e.g., 8.97 kHz) transmitter coil, the second transmission coil 62 comprises a second frequency (e.g., 7 kHz) transmitter coil, the first receive coil 61 comprises a first frequency receive coil, and the second receive coil 63 comprises a first/second frequency (7/8.97 kHz based on the noted first and second frequency examples) receive coil.

As will be appreciated by one having ordinary skill in the art, the dual functionality of the second receive coil 63 reduces the number of receive coils, thereby reducing the number of attachments to a patient simplifying system design, and reducing power requirements.

In some embodiments of the invention, each receive coil 61, 63 is adapted to receive transmissions from each of the transmission coils 60, 62. As discussed in detail below, the dual functionality of both receive coils 61, 63 enhances the accuracy of anatomical measurements determined from transmissions by and between the coils 60-63.

Figure 8:
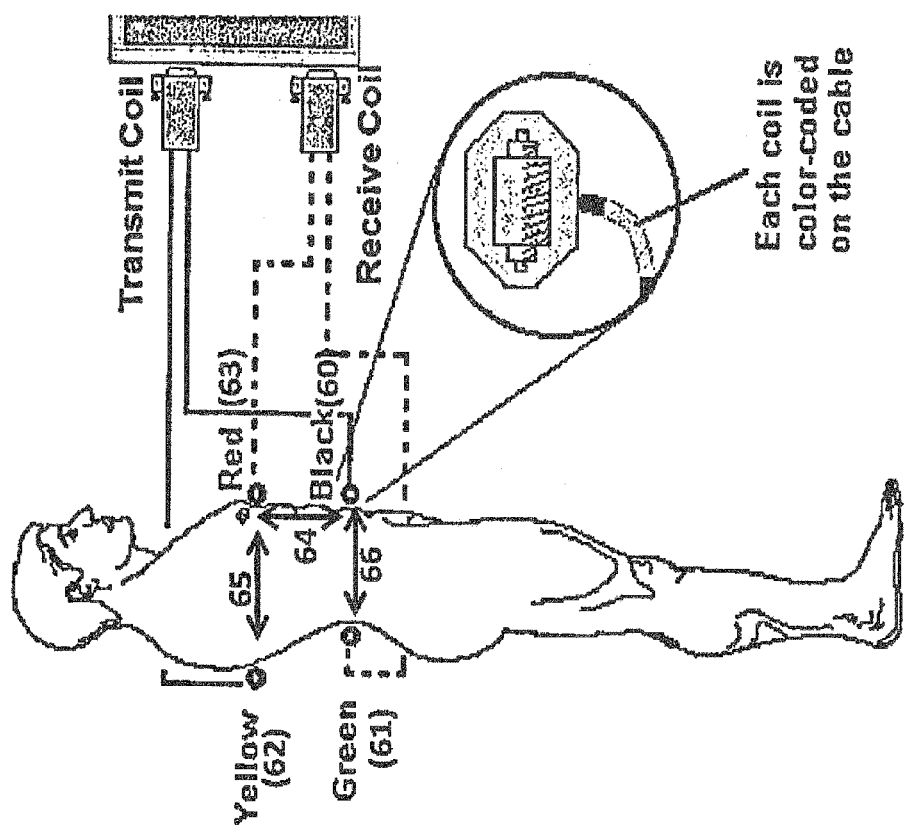
FIG. 8 is a schematic illustration of one embodiment of a pulmonary ventilation system of the invention.

Referring now to FIG. 8, there is shown the positioning of the coils 60-63 on a subject, in accordance with one embodiment of the invention. As illustrated in FIG. 8, the first transmission coil 60 is positioned on the front of the subject proximate the umbilicus of the subject and the first receive coil 61 is preferably positioned at the same axial position, but on the back of the subject. The second receive coil 63 is positioned on the front of the subject proximate the base of the sternum of the subject and the second transmission coil 62 is located at the same axial position, but on the back of the subject.

According to the invention, the positions of the transmission coils 60, 62 and receive coils 61, 63 can be reversed, i.e. transmission coil 60 and receive coil 63 placed on the back of the subject and transmission coil 62 and receive coil 61 placed on the front of the subject.

As discussed in detail below, both transmission coils 60, 62 can also be placed on the front or back of the subject and the receive coils 61, 63 can be placed on the opposite side.

As stated, in one embodiment of the invention, the second receive coil 63 is adapted to receive and process signals from both the first and second transmission coils 60, 62, reducing the number of coils required to determine $V_T$ (using a "three-degrees-of-freedom" model of the invention) from six to four. This simplifies the instrumentation attached to a subject, and reduces the power requirements of the system 20. If the device is used only to measure changes in body position, coils 61 and 62 are eliminated, thereby further reducing power requirements and simplifying the embedded software.

According to the invention, the coils 60-63 can be attached to the subject by various suitable means. In one embodiment of the invention, the coils 60-63 are attached to the subject via medical tape or a vest.

Referring back to FIG. 8, arrow 64 represents the Xi or, in this instance, the xiphi-umbilical distance. Arrow 65 represents the rib cage-anteroposterior (RC-AP) distance, while arrow 66 represents the abdomen-anteroposterior (Ab-AP) distance.

FIG. 8 thus illustrates the three-degrees of freedom or motion (RC-AP, Ab-AP, and Xi) that are measured in accordance with the invention. According to the invention, as the subject or patient breathes, the change in distance between each pair of coils 60, 61 and 62, 63 and 60, 63 (denoted by arrows "65", "66", and "64") is sensed. The change in distance between the paired coils corresponds to changes in voltage that is a function of changes in the anteroposterior distance of the rib cage (RC-AP) and the abdomen (Ab-AP) and axial displacement of the chest wall (Xi).

Simultaneously, the body position and the axial displacement of the chest wall (denoted by arrow "64"), e.g., xiphi-umbilical distance (Xi), are measured. In one embodiment of the invention, wherein coil 63 comprises a dual functionality coil, the axial displacement of the chest wall is directly determined from sensed changes in voltage between transmission coil 60 and receive coil 63.

In one embodiment of the invention, wherein receive coils 61 and 63 comprise dual functionality coils, the axial displacement of the chest wall is similarly determined from sensed changes in voltage between transmission coil 60 and receive coil 63.

As will also be readily appreciated by one having ordinary skill in the art, the use of two dual functionality receiver coils, e.g., receive coils 61, 63, and the placement thereof on one side of the subject facilitates simple and accurate determination of axial displacement of the chest wall, regardless of the axial placement of the receive coils 61, 63 (provided, the receive coils 61, 63 remain substantially axially aligned).

The use of two dual functionality receiver coils, e.g., receive coils 61, 63, and the placement thereof on one side of the subject also facilitates accurate determination of whether a measured displacement of the rib cage actually reflects true ventilation of a subject.

According to the invention (and discussed in detail below), the acquired data representing the noted measured distances is employed by the ventilation parameter program 38 of the invention to determine one or more ventilation parameters or characteristics.

Referring back to FIG. 7 in the illustrated embodiment, a first transmission signal pre-processor 70 transmits a signal to the first transmission coil 60. Similarly, a second transmission signal processor 72 transmits a signal to the second transmission coil 62.

The received signals are then processed by three channels, including a first detection circuitry channel 80, a second detection circuitry channel 82, and a third detection circuitry channel 84. The output of the individual channels is preferably transmitted to the data input interface circuitry 24 for subsequent processing and storage by the CPU 28, in accordance with the executable programs 30 stored in memory 31.

The data acquisition circuitry 21 also includes a flow meter 86, whose output is preferably processed by a low pass filter 88 before being transmitted to the data input interface circuitry 24. The data provided by the flow meter 86 is employed during the calibration step, as discussed below.

Figure 9:
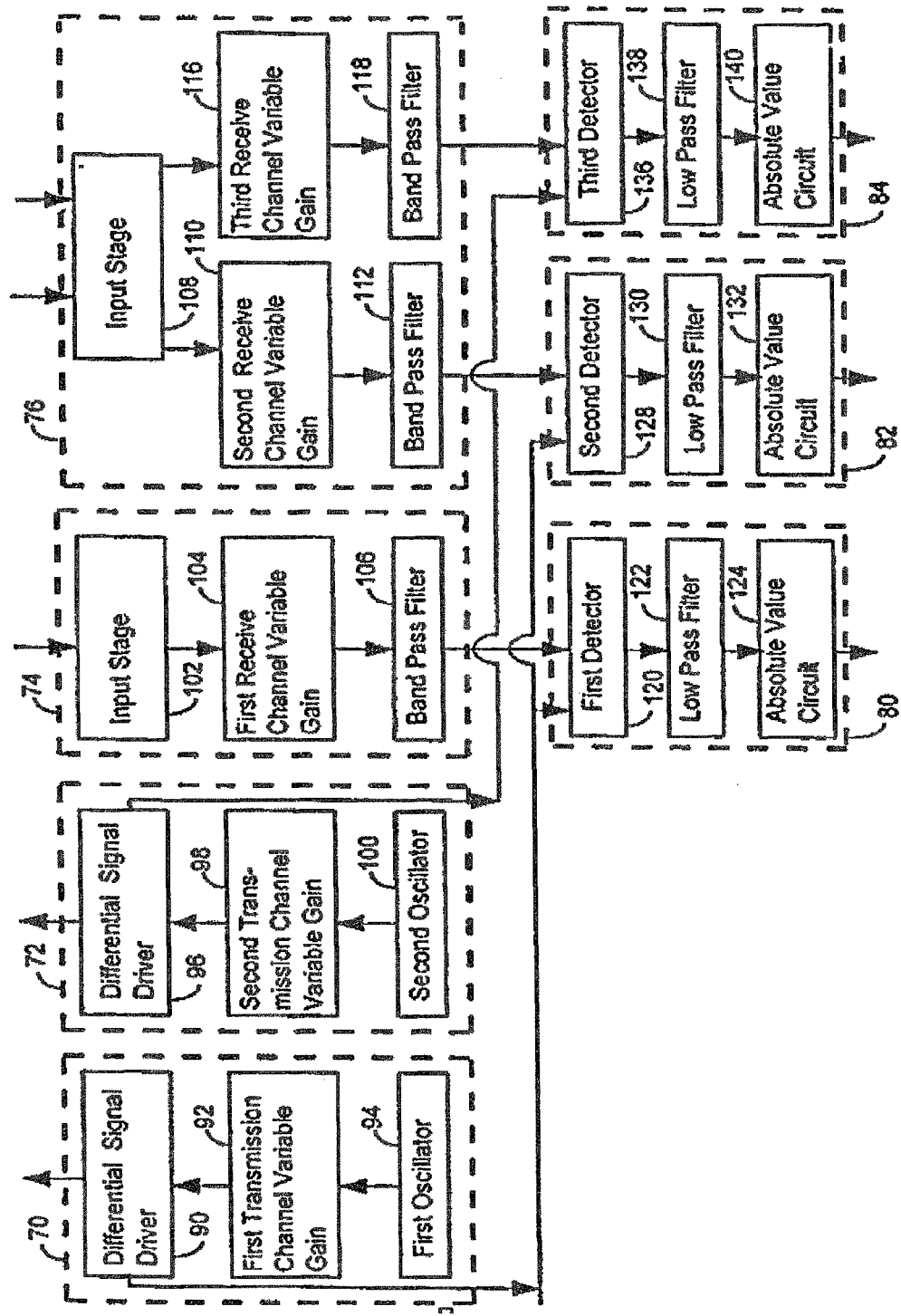
FIG. 9 is a schematic illustration of the data acquisition circuitry shown in FIG. 7 of the invention.

Referring now to FIG. 9, there is shown a more detailed view of selected components of the data acquisition circuitry 21, in accordance with one embodiment of the invention. As illustrated in FIG. 9, the data acquisition circuitry 21 includes a first transmission signal pre-processor 70 having a first oscillator 94. In one embodiment, the first oscillator 94 is set to 8.97 kHz.

According to the invention, the oscillator signal is transmitted to a first transmission channel variable gain circuit 92, which allows an optimal gain value to be set. The gain adjusted signal is then transmitted to a differential signal driver 90, and is then transmitted to the first transmission coil 60.

As illustrated in FIG. 9, the output from the differential signal driver 90 is also transmitted to the first channel detection circuitry 80 and the second channel detection circuitry 82, as will be discussed further below.

The second transmission signal-processor 72 operates in a similar manner. According to the invention, the second oscillator 100 oscillates at a pre-determined frequency, e.g., 7 kHz. The oscillator signal is transmitted to a second transmission channel variable gain circuit 98, which is independently set for an optimal gain value. The gain adjusted signal is then transmitted to a differential signal driver 96, and is then transmitted to the second transmission coil 62. The output of the differential signal driver 96 is also transmitted to the third channel detection circuitry 84, as will be discussed further below.

As illustrated in FIG. 7, the signal from the first transmission coil 60 is processed by the first receive coil 61 and is then transmitted to the first received signal pre-processor 74. As illustrated in FIG. 9, the first signal pre-processor 74 can be implemented with an input stage 102, a first receive channel variable gain 104, and a band pass filter 106.

According to the invention, the variable gain 104 can be set through the data input interface circuitry 24 to optimize the signal-to-noise ratio. Preferably, the band pass filter 106 is set to reduce noise above and below 8.97 KHz.

As illustrated in FIG. 7, the second received signal pre-processor 76 operates in a similar manner. However, as indicated above, the second receive coil 63 is preferably adapted to process two signals. The second received signal pre-processor 76 accordingly processes two signals.

As illustrated in FIG. 9, a single input stage 108 processes the two signals and transmits the output to two channels in communication with the input stage 108. Each channel includes a variable gain circuit 110/116 and a band pass filter 112/118.

According to the invention, the separate gain controls 92, 98, 104, 110, 116 are preferably optimized to increase the signal-to-noise ratio. The gain controls 92, 98 for the transmitted signal can also be optimized to minimize power requirements.

Since the gain for the transmitted signal can be changed independently of the gain of the receiver channel, the signal-to-noise ratio can be improved, while minimizing the magnetic field exposure at skin surface of the patient.

According to the invention, the band pass filters 106, 112, 118 are adapted to minimize interference from extraneous magnetic fields and noise sources. As illustrated in FIG. 9, the output from the first received signal preprocessor 74 is transmitted to the first channel detection circuitry 80. The circuitry 80 preferably includes a first detector 120, which is set to the frequency established by the first oscillator 94. The output of the first detector 120 is transmitted to a low pass filter 122 and an absolute value circuit 124. The signal is then transmitted to the data input interface circuitry 24 for processing by the CPU 28.

The second channel detection circuitry 82 operates in a similar manner. The second detector 128 is set to the frequency established by the first oscillator 94 and processes the signal from the second receive channel band pass filter 112. The second channel detection circuitry 82 includes a low pass filter 130 and an absolute value circuit 132 to produce a data signal that is also transmitted to the CPU 28 for processing, in accordance with the executable programs 30 stored in memory 31.

The third channel detection circuitry 84 is set to the frequency established by the second oscillator 100 and processes the signal from the third receive channel band pass filter 118. The third receive channel detection circuitry 84 also includes a third detector 136, a low pass filter 138 and an absolute value circuit 140.

Processing associated with the executable programs 30 stored in memory 31 will now be described in detail.

According to the invention, the calibration program or routine 32 determines calibration coefficients, i.e. volume-motion coefficients, throughout a range of body positions and activities. Calibration coefficients are then derived for specific activities or body postures, i.e. sets of calibration coefficients. These different sets of calibration coefficients are then applied to selected regions of the acquired data set.

The calibration routine 32 thus allows the user to employ volume-motion coefficients from different segments of the data set (e.g., sitting, standing, walking, sleeping supine, sleeping prone, etc.). These coefficients can then be applied to the data set to construct spirograms of volume over time.

In some embodiments of the invention, the calibration program 32 is also adapted to "automatically" select derived volume-motion coefficients, i.e. a volume-motion coefficient data set, reflecting a specific body position (or posture) or activity when a subject or patient is in the noted body position or performing the activity. In the noted embodiments, the calibration program 32 would automatically select a volume-motion coefficient data set in response to a transmitted body posture-motion signal from a position detector 30B.

As will be appreciated by one having ordinary skill in the art, various sensors can be employed within the scope of the invention to sense and transmit the body posture-motion signal, e.g., 3-axis accelerometer. In one embodiment of the invention, the calibration program 32 is responsive to a signal reflecting the axial displacement of the chest wall, e.g., change in the sternal or xiphi-umbilical distance.

According to the invention, a voltage spike detector 30A detects transient spikes of Xi voltage to determine a change in position and subsequent values of end-expiratory Xi are assessed and used to determine the specific position by a body position detector 30B.

As will be appreciated by one having ordinary skill in the art, this eliminates the need for any other sensors used to detect changes in body position, reduces power requirements and eliminates the need and cost of an attendant/observer.

As discussed in detail in the Examples section, the calibration routine 32 facilitates the accurate determination of the volume of air inhaled and exhaled; the volume, i.e. $V_T$, being determined from the sum of three signals (the changes in the axial dimensions of the anteroposterior diameter of the rib cage (RC) and abdomen (Ab) and the changes in the axial dimensions of the anterior chest wall).

In accordance with one embodiment of the invention, the calibration maneuver includes having a subject breathe through a flow meter, e.g., flow meter 86, for 1-2 minutes at varied tidal volumes and body positions.

In some embodiments of the invention, the calibration program 32 is also used to adjust the variable gain elements 92, 98, 104, 110, and 116 for optimum signal levels.

As indicated above, in one embodiment, the element analysis program 36 is adapted to perform element analyses on acquired signals (representing acquired data) to reduce any extraneous noise in the signals. In one embodiment of the invention, the element analyses includes at least one Fourier analysis, which, combined with band pass filtering in the software, facilitates use of the system 20 in ambulatory activities.

In one embodiment of the invention, the ventilation parameter program 38 correlates the three-degrees-of-freedom data with the flow meter data. The parameter program 38 then employs the data to create correlation parameters for determining ventilation parameters or characteristics, including end-expiratory, lung volume, breathing frequency, total pulmonary ventilation, inspiratory breathing time, expiratory breathing time, and total breathing time. These parameters can then be displayed on an integral visual output device or transmitted wirelessly to an external receiver and/or display device.

Figure 10:
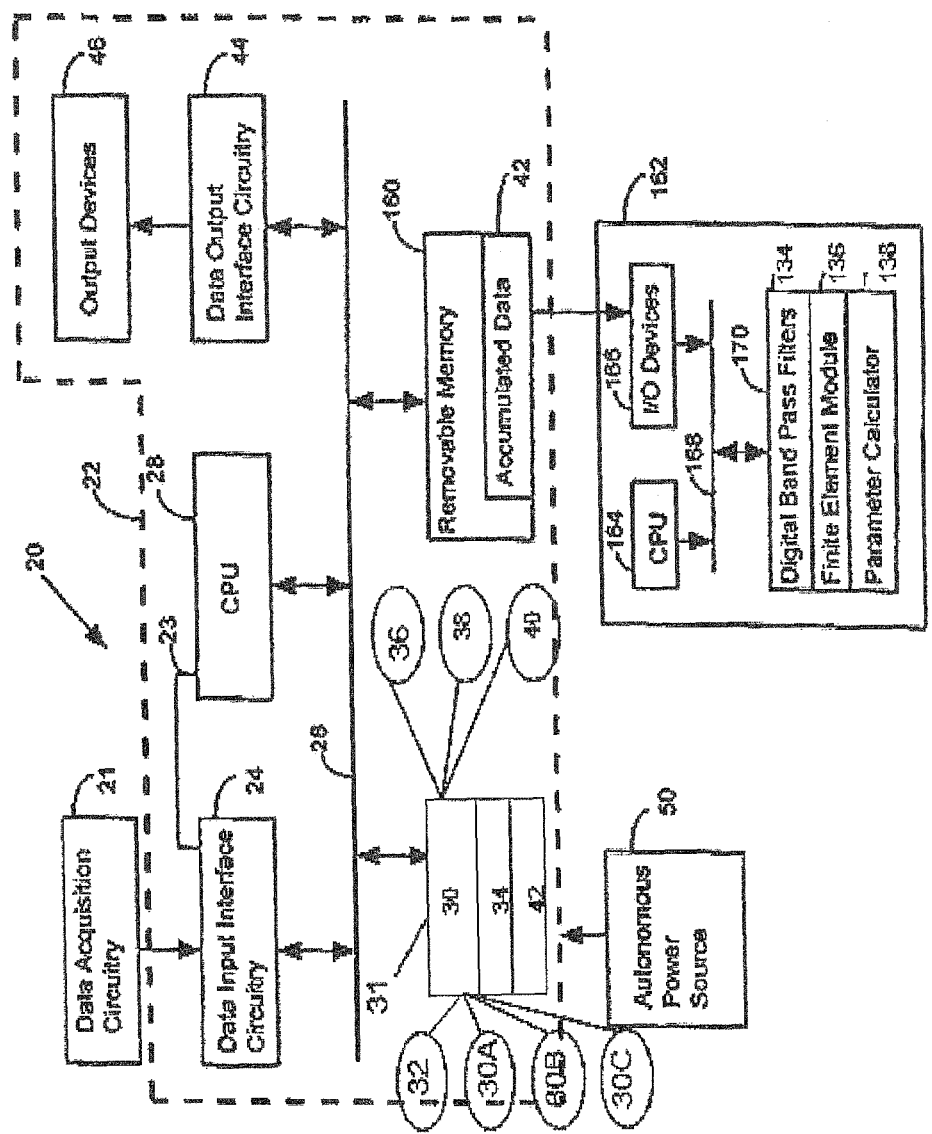
FIG. 10 is a schematic illustration of one embodiment of a pulmonary ventilation system of the invention.

Referring now to FIG. 10, there is shown another embodiment of the pulmonary ventilation system 20 of the invention. In this embodiment, the power source 50 is external to the data processing circuitry 22. Further, the pulmonary ventilation system 20 includes a removable memory 160 (e.g., a flash memory card), which is employed to store the accumulated data 142. The accumulated data 142 can then be transferred to a receiving station, such as a personal computer 162 or wirelessly transmitted in "real time".

In the illustrated embodiment, the personal computer 162 includes a central processing unit 164 and a set of input/output devices 166, which communicate via bus 168. The system 20 also includes memory 170, which is in communication with bus 168. As illustrated in FIG. 10, the memory 170 includes at least one, more preferably, a plurality of executable programs 150, and digital band pass filters 134, which are used post-data acquisition to further refine accumulated data 142 and analyze body position and breathing pattern. In one embodiment of the invention, the executable programs 150 include a calibration program (or routine) 152, a voltage spike detector 130A, a body position detector 130B, a volume calculator 130C, a signal processing or element analysis program 154, a ventilation parameter program 156, and an output program 158. As discussed above, the calibration program (or routine) 152, voltage spike detector 130A, body position detector 130B, volume calculator 130C, signal processing or element analysis program 154, ventilation parameter program 156 and output program 158 perform similar functions as to the calibration program (or routine) 32, voltage spike detector 30A, body position detector 30B, volume calculator 30C, signal processing or element analysis program 36, ventilation parameter program 38 and output program 40, respectively, but are located in a different platform, for example, in a personal computer 162.

As will be readily appreciated by one having ordinary skill in the art, this system facilitates processing of the accumulated data 142 with a separate device.

EXAMPLES

The following examples are given to enable those skilled in the art to more clearly understand and practice the present invention. They should not be considered as limiting the scope of the invention, but merely as being illustrated as representative thereof.

Example 1

Thirty subjects (10 non-obese awake (BMI=25.7±3.4 kg/m2 (mean±SD), 10 obese awake (BMI=46.7±9.1 kg/m2) and 10 obese (BMI=45.7±1.0 kg/m2) with sleep apnea napping) were studied in the supine, left lateral, and right lateral sleep positions.

The non-obese, awake subjects comprised seven 7 males and three 3 females, age 28-49 yr. (mean age 30.2 yr). The obese, awake subjects comprised six 6 males and 4 females, age 24-64 yr. (mean age 44.4 yr). The obese, napping subjects comprised 5 males and 5 females, age 28-60 yr. (mean age 42.2 yr).

Device and Measurements

The anteroposterior displacements of the rib cage and abdomen, as well as the axial displacements of the chest wall (i.e. Xi) were measured using a light-weight, portable pulmonary ventilation system of the invention (also referred to herein as a magnetometer system or device) using the "three-degrees-of-freedom" model set forth in Eq. 5 above. Signals were sampled at 20 Hz and stored to compact flash memory.

Calibration was performed with subjects in the supine, right lateral and left lateral decubitus positions.

Protocol

The non-obese and obese awake subjects were studied while in the supine, right lateral and left lateral decubitus positions (hereinafter "test positions"). After calibration, each subject breathed through a mouthpiece connected to a spirometer (PK Morgan Ltd®.). Subjects were instructed to take breaths ranging from 0.5 to 2.5 L. At least 15 breaths (average 25.6 breaths) of varied volumes were obtained from each subject in each position. Data was simultaneously collected using a ventilation or magnetometer system of the invention, such as system 20 described above.

Figure 11:
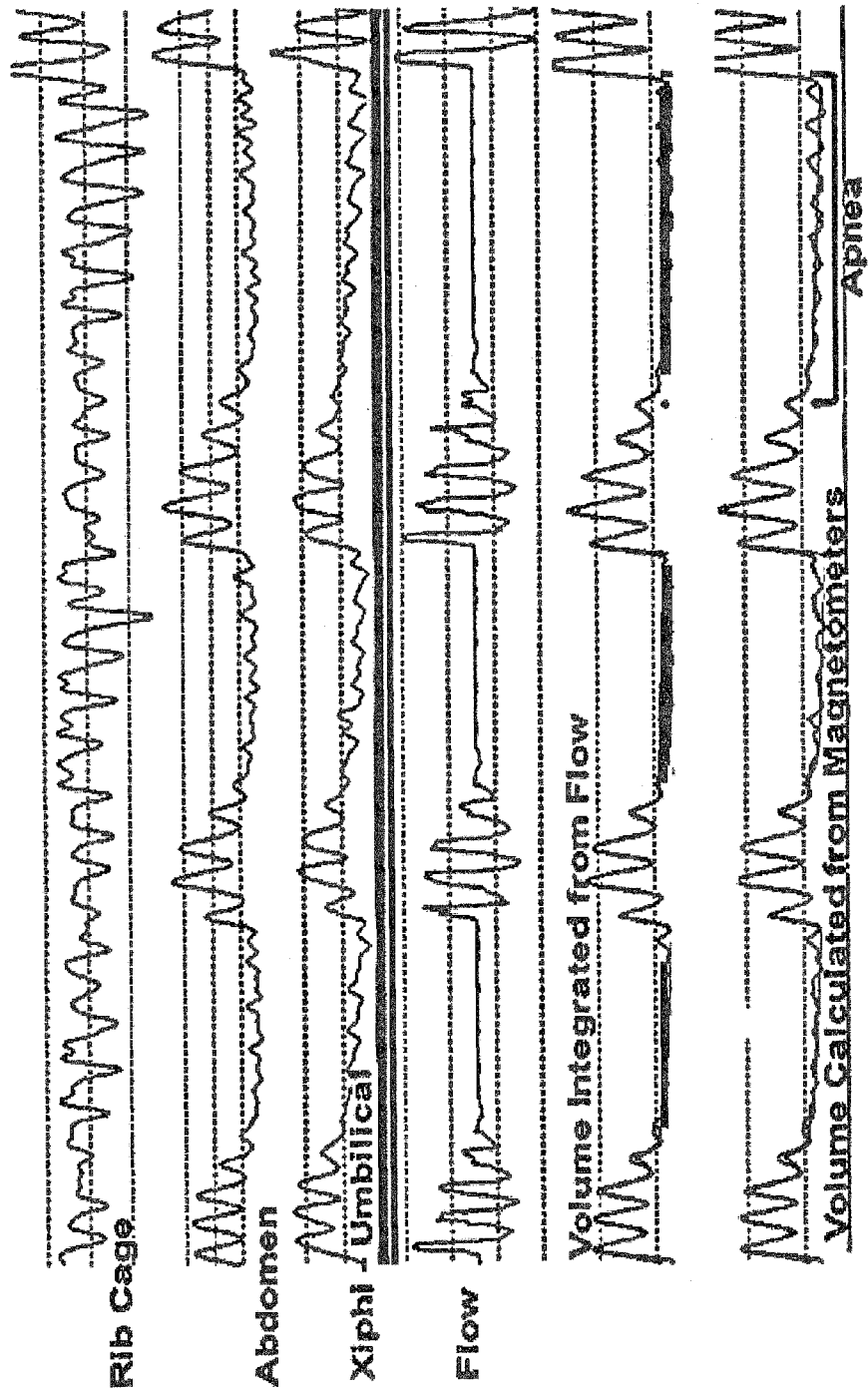
FIG. 11 is an example of an apnea and hypopnea determined by pneumograph (flow meter: gold standard) and by magnetometry in an obese individual during a nap.

The daytime nap studies were done using a tight-fitting facemask equipped with a pneumotachograph applied to cover the nose and mouth. Subjects were observed while sleeping in a quiet room. Each subject was monitored continuously and changes in position were recorded. Data was collected simultaneously using the magnetometer system. As illustrated in FIG. 11, apneas and hypopneas were identified using pneumotachography and magnetometry, and it is noted of the nearly identical tracing for volume determined from the flow meter and with magnetometry.

Statistical Analysis

The coefficient of determination ($R^2$) was calculated for $V_T$, $T_I$ and $T_E$ derived from the simultaneous spirometer or pneumotachograph and magnetometer signals using a linear correlation model. This analysis was performed for individual subjects in each position and for pooled data from all subjects in all positions. The mean percent differences (% difference) between the spirometer or pneumotachograph and magnetometer derived measurements ($V_T$, $T_I$, and $T_E$) were also calculated.

The methods set forth in Bland and Altman, "Statistical Methods for Assessing Agreement Between the Two Methods of Clinical Measurement", Lancet, vol. 1, pp. 307-310 (1986), which is incorporated by reference herein, were used to assess the agreement between measurements obtained from the spirometer and magnetometer or pneumotachograph and magnetometer.

Results

There were significant correlations between the spirometer and magnetometer measurements of $V_T$.

For pooled data of all non-obese subjects in all positions, a total of 645 breaths were analyzed. As illustrated in FIG. 12, the $R^2$ values for $V_T$, $T_I$, and $T_E$ were 0.94, 0.89, and 0.91, respectively.

For pooled data of all awake obese subjects in all positions, a total of 892 breaths were analyzed. As illustrated in FIG. 12, the $R^2$ values for $V_T$, $T_I$, and $T_E$ were 0.95, 0.96, and 0.97, respectively.

The absolute mean % differences for $V_T$, $T_I$ and $T_E$ for from pooled data were 9.0±7%, 7.5±7%, and 6.4±6% (mean±SD), respectively for the awake subjects.

There were also significant correlations between the pneumotachograph and the magnetometer measurements during daytime naps for the obese subjects.

Figure 13:
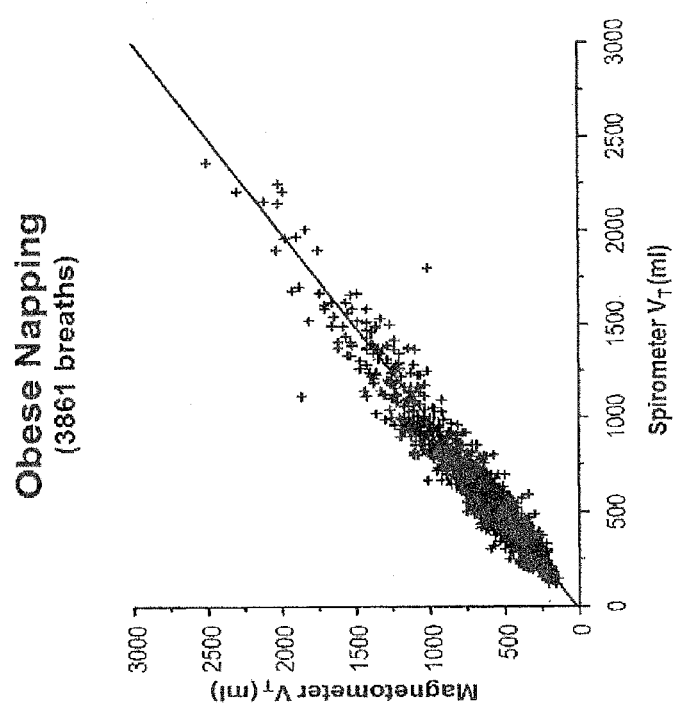
FIG. 13 demonstrates the relationship between magnetometer and pneumotach derived tidal volumes for obese sleeping individuals.

For $V_T$, a total of 3861 breaths were analyzed. For $T_I$ and $T_E$, 65 randomly selected breaths were analyzed from each subject (n=650 breaths). As illustrated in FIG. 13, the $R^2$ values for $V_T$, $T_I$ and $T_E$ were 0.94, 0.95, and 0.95, respectively.

The absolute mean % differences for $V_T$, $T_I$ and $T_E$ pooled data for the obese napping subjects were 9.1±8%, 8.9±8%, and 6.6±5%, respectively.

Figure 14:
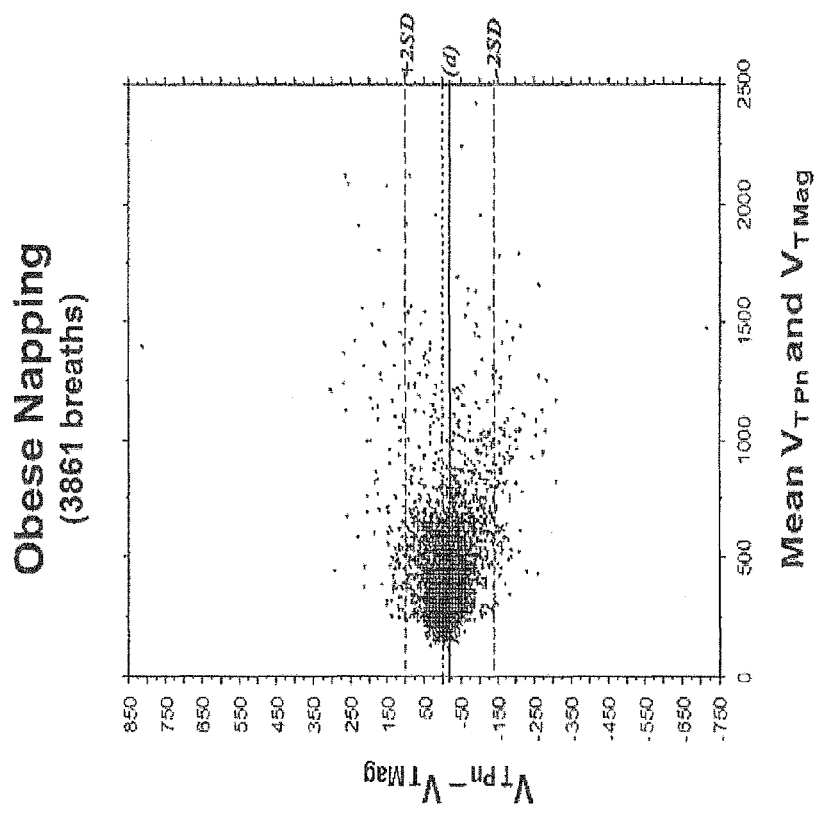
FIG. 14 The differences between $V_{T\ Mag}$ and $V_{T\ Pn}$ are plotted against their mean for 10 obese sleeping subjects (n=3861 breaths). The mean difference between $V_{T\,Mag}$ and $V_{T\,Pn}$ is depicted by the solid line and the 95% confidence intervals by the dashed lines (±2SD). The interval representing the "limits of agreement" by Bland and Altman methods.

Using the Bland, et al. methods, agreement between the magnetometer and spirometer or pneumotachograph values for $V_T$ ($V_{T\,Mag}$ and $V_{T\,Spiro}$ or $V_{T\,Pn}$), $T_I$ ($T_{I\,Mag}$ and $T_{I\,Spiro}$ or $T_{I\,Pn}$), and $T_E$ ($T_{E\,Mag}$ and $T_{E\,Spiro}$ or $T_{E\,Pn}$) for subjects in the above different groups was assessed. The mathematical mean differences (d) between $V_{T\,Spiro}$ and $V_{T\,Mag}$, and the 95% confidence intervals (reflecting bias) for the napping obese subjects is illustrated in FIG. 14.

The mathematical mean difference for the non-obese awake subjects in all positions was 26.4 ml with a standard error (SE) of 6.8 ml. The means for $V_{T\,Spiro}$ and $V_{T\,Mag}$ for this data set were 1177.3 ml and 1150.9 ml, respectively.

For the obese awake subjects, the mathematical mean difference was −13.5 ml with a SE of 4.0 ml. The means for $V_{T\,Spiro}$ and $V_{T\,Mag}$ for this data set were 868.0 ml and 881.5 ml, respectively.

The mathematical mean difference between $V_{T\,Pn}$ and $V_{T\,Mag}$ for the obese sleeping subjects was −17.7 ml with a SE of 1.0 ml. Mean $V_{T\,Pn}$ and $V_{T\,Mag}$ for this group were 460.7 ml and 478.4 ml, respectively.

The limits of agreement for $V_T$ are clinically acceptable (e.g. ±20-30% of $V_T$). As evidenced by the graphical illustrations shown in FIG. 14, most of the data is aggregated around zero with a minor percentage scattered peripherally. This scattering of data over the higher ranges of $V_T$ increases the limits of agreement.

This peripheral scatter is primarily due to three factors. First, the range of $V_T$ studied was wide during wakefulness (e.g., for group 1, $V_T$ ranged from 250 to 4100 ml), as the subjects were instructed to take occasional deep breaths. The inaccuracies over this range of volume may be due to the lesser range of $V_T$ encountered during sleep.

Second, some of the measurements that were scattered peripherally may represent accidental manual errors in measurements from the spirometer or pneumotachograph. Third, the effect of the facemask on $V_T$ may have increased $V_T$ in our sleeping subjects.

Nonetheless, as will be appreciated by one having ordinary skill in the art, the agreements and bias are accurate enough to be clinically relevant.

Example 2

Subjects

The following study was conducted to assess the accuracy of the "three-degrees-of-freedom" model of the invention and a pulmonary ventilation or magnetometer system employing the subject model to detect apneas and hypopneas during sleep.

Fifteen subjects (10 males and 5 females) with variable degrees of clinical suspicion for obstructive sleep apnea (OSA) were selected for the study. The mean age for the group was 45.5±12.5 years (mean±SD). The mean body mass index for the group was 35.0±5.7 kg/m².

Device and Measurements

The anteroposterior displacements of the rib cage and abdomen, as well as the axial displacements of the chest wall (i.e. Xi) were similarly measured using a light-weight, portable pulmonary ventilation system of the invention (also referred to herein as a magnetometer system or device) using the "three-degrees-of-freedom" model set forth in Eq. 5 above.

Two pairs of electromagnetic coils, each ~½" in diameter, were employed to measure three-degrees of chest wall motion. The coils were attached as shown in FIG. 8.

Signals were sampled at 20 Hz and stored to compact flash memory. A pneumotachograph was also attached to the magnetometer system for calibration.

Calibration was performed with subjects in the supine, right lateral and left lateral decubitus positions. Each subject was instructed to breathe through the pneumotachograph with breaths of varied depth for greater than 1 min. Free movements of the upper and lower extremities were also encouraged during the calibration process (i.e. flexion and extension of the hip, knee, elbow and shoulder joints).

Multiple linear regression of the change in each chest wall dimension, with the corresponding tidal volume integrated from the pneumotachograph, was performed to obtain the volume-motion coefficients of Eq. 5.

Protocol

After calibration in the supine, right lateral and left lateral decubitus positions (hereinafter "test positions"), continuous recording of the magnetometer signals was performed throughout a 12 lead polysomnography (PSG).

Figure 15:
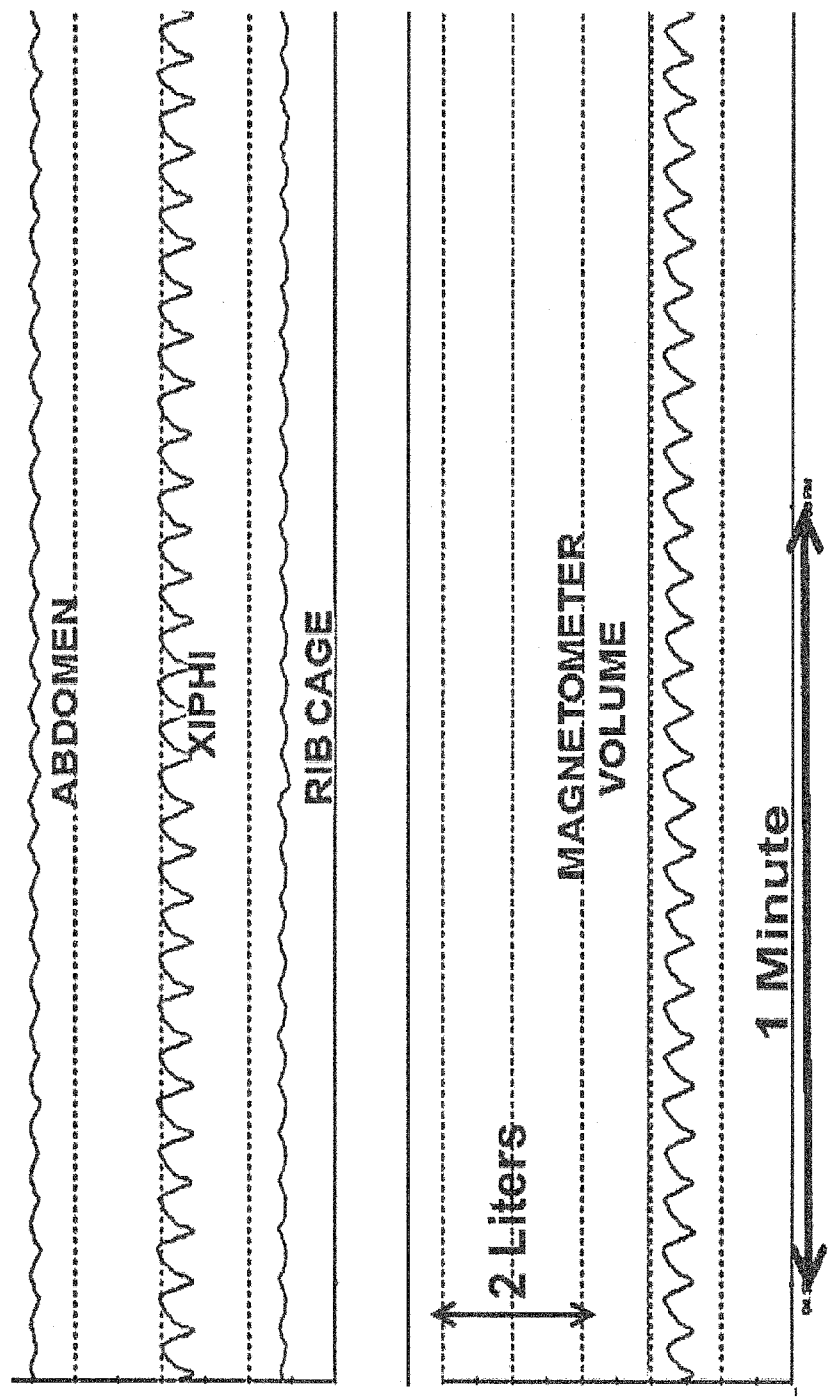
FIG. 15 is a graphical illustration of magnetometer derived volume for an obese subject demonstrating no apneas or hypopneas during sleep according to the invention.
Figure 16:
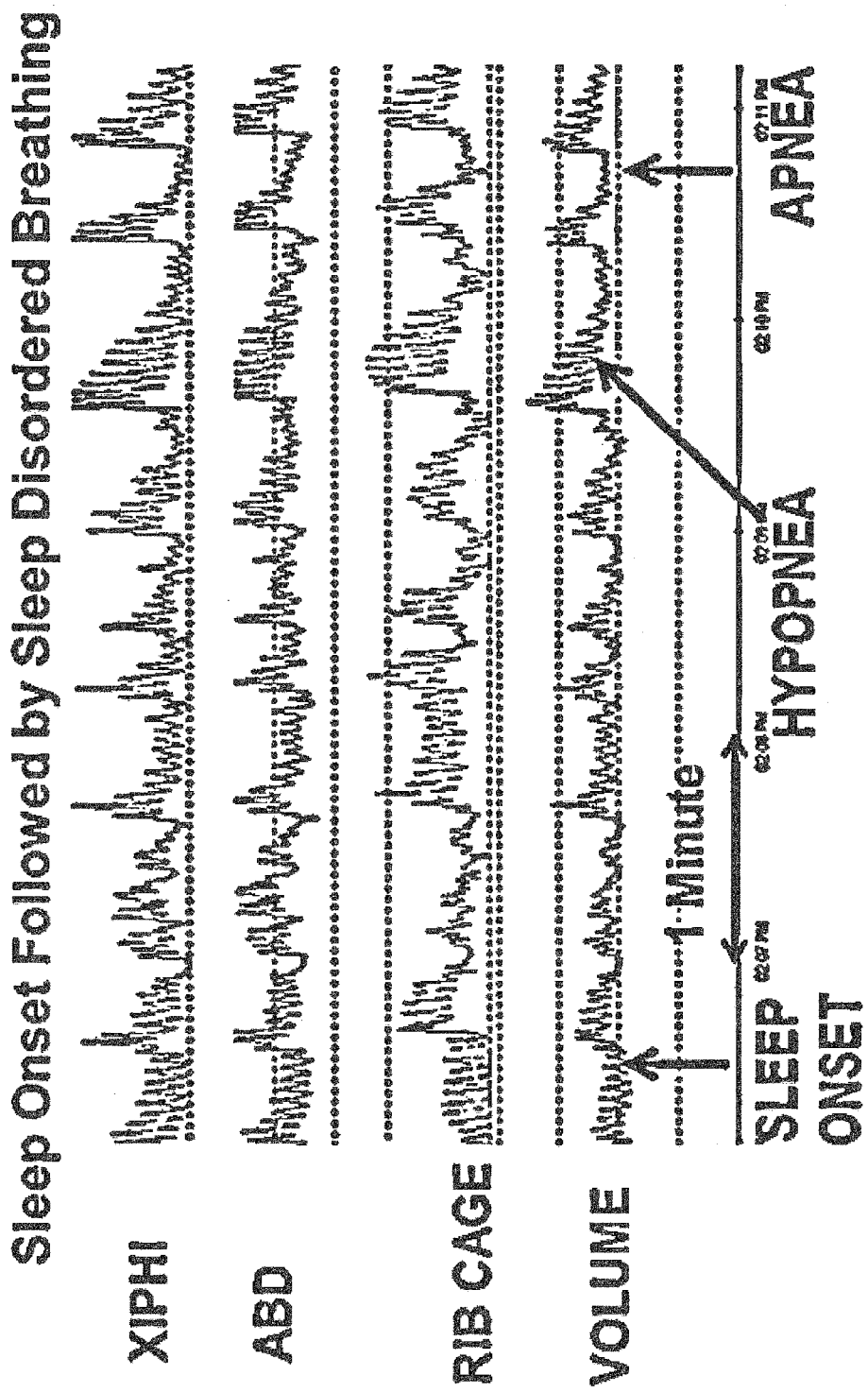
FIG. 16 is an exemplar recording of the implementation of the 3 degrees of freedom model to detect apneas and hypopneas in a sleeping individual in a given body position.

Exemplar recordings of magnetometer signals and associated derived tidal volume are shown in FIGS. 15 and 16. Quiet breathing of a subject during sleep with no apneas or hypopneas is reflected in FIG. 15. Sleep onset of a subject followed by hypopneas and apneas is reflected in FIG. 16.

Scoring of the magnetometer data was conducted in 30 second intervals. No oxygen saturation or EEG arousals were employed in the scoring process.

Scoring comprised polysomnography (PSG) scores and the magnetometer system signals (or scores). Apnea and hypopnea indices (AHI), apnea indices (AI) and hypopnea indices (HI) were also recorded.

A respiratory event (i.e. apnea or hypopnea) or occurrence was defined as ≥50% reduction in $V_T$ with a trend that was sustained for ≥10 seconds. Apneas were identified when the volume tracing was almost flat (minor oscillations were ignored). Hypopneas were identified when the volume could be measures (i.e. >120 cc).

Statistical Analysis

The mean apnea, hypopnea count and indices were compared using the standard t-test. Means±standard deviation (mean±SD) was also determined.

Results

No significant differences were noted between the PSG scores and the MTG scores for the apnea and hypopnea index (AHI), apnea index (AI) and hypopnea index (HI). The mean±SD AHI for the PSG and MTG data were 38.9±30.5 and 42.5±27.9, respectively.

Referring now to FIG. 4, there is shown a graphical illustration of the apnea and hypopnea indices (AHI) for all fifteen subjects. The dashed lines in FIG. 4 represent the limits of severity of sleep apnea, i.e. AHI 5-15 deemed mild sleep apnea, >15-30 deemed moderate sleep apnea, and >30 deemed severe sleep apnea.

As illustrated in FIG. 4, there was significant agreement in severity between PSG and MTG scores.

There were no significant differences in the mean±SD apnea index for the PSG and MTG data (13.6±13.3 and 13.8±10.0, respectively) and the mean±SD hypopnea index data (25.6±20.3 and 28.8±19.5, respectively).

There was also significant agreement in the severity of sleep apnea (i.e. AHI 5-15 deemed mild, >15-30 deemed moderate, and >30 deemed severe) between the MTG and PSG scores. As reflected in FIG. 4, only two subjects had a change in the AHI from mild (i.e. 5.4/hr.) to moderate (i.e. 17.7/hr.), i.e. subject #13 (shown in parentheses) and from moderate (i.e. 28.7/hr.) to severe (41.3/hr.), i.e. subject #6, respectively.

Figure 17:
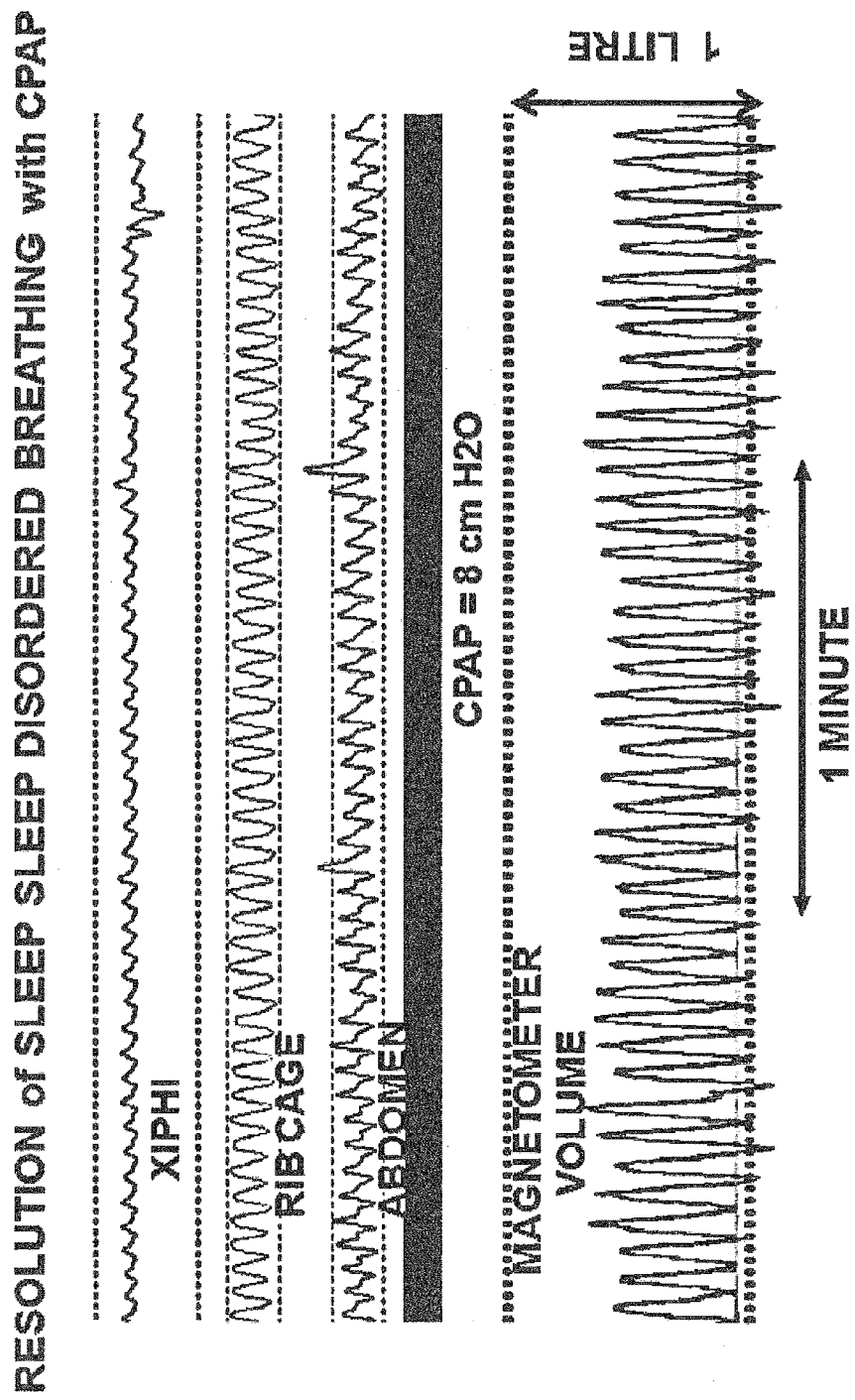
FIG. 17 is an exemplar recording of the implementation of the 3 degrees of freedom model to demonstrate the beneficial effects of CPAP eliminating the apneas and hypopneas the sleeping individual depicted in FIG. 16.

This study thus demonstrates that the "three-degrees-of-freedom" model of the invention and a magnetometer system employing the subject model can accurately and readily detect apneas and hypopneas during sleep. As illustrated in FIG. 17, the system can also readily establish the severity of sleep apnea and demonstrate effect CPAP treatment.

Example 3

The following study is an example of the use of the pulmonary ventilation system and method to simultaneously determine body position and breathing during sleep.

One obese subject referred for evaluation of sleep apnea with overnight polysomnography was studied. The anteroposterior displacements of the rib cage (RC) and abdomen (Ab), as well as the axial displacements of the chest wall (Xi) were measured using the ventilation system of the invention (FIG. 18). Body position was measured using axial displacements (Xi).

After calibration in the supine, prone, right lateral and left lateral decubitus positions, continuous recording of the magnetometer signals was performed throughout an overnight 12 lead polysomnography test including video-recording body position.

The overnight recordings of magnetometer signals and body position are shown in FIG. 18. As detailed in the method of the invention, a transient voltage spike heralds a change in body position. The new body position is identified by the following stable end-expiratory voltage. The study subject slept in the supine (S), left lateral (L), and right lateral (R) body position. There was one awakening (A) where the subject remained in bed and two awakenings where the subject went to the bathroom (O). The low voltage oscillations in the RC, Ab and Xi panels (which are better appreciated when expanding the time scale) represent tidal breathing and are used to calculate tidal volume using the three-degrees of freedom model.

As will be appreciated by one having ordinary skill in the art, the "three-degrees-of-freedom" models of the invention and ventilation (or magnetometer) systems employing the models can be readily employed to accurately and simultaneously determine body position and ventilation parameters or characteristics, including total pulmonary ventilation, breathing frequency, inspiratory breathing time, expiratory breathing time and total breathing time. The noted ventilation parameters can be employed to identify normal breathing patterns at rest (while awake and during sleep) and during activities, with changes in posture, with exposure to pollutants, or to identify abnormal breathing patterns or respiratory events, such as those presented with respiratory dyskinesia, impending respiratory failure, exacerbations of emphysema, asthma and other forms of lung disease.

The ventilation parameters can also be readily employed to detect and characterize obstructive and central apneic episodes in adults and infants during sleep, calculate flow volume loops during exercise and sleep, characterize breathing patterns in individuals with undiagnosed causes of dyspnea, and determine the effects of air toxins on pulmonary and cardiovascular health.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

Although the present invention has been shown and described with respect to several preferred embodiments thereof, various changes, omissions and additions to the form and detail thereof, may be made therein, without departing from the spirit and scope of the invention.

What is claimed is:

1. A method of simultaneously monitoring body position and respiration of a subject, comprising the steps of:
   (i) monitoring a subject orientation by data acquisition circuitry,
   (ii) monitoring an end-expiratory value of an axial dimension of a distance Xi between a first location and a second location for said subject orientation by said data acquisition circuitry,
   (iii) assigning a body position for said end-expiratory value for said subject orientation during a calibration maneuver in which said subject is asked to assume varied body positions by a processor,
   (iv) determining when said subject orientation changes body position by said processor, wherein a detector is used for measuring transient position-induced voltage spikes provided by said processor, (v) determining, an end-expiratory value that is stable following said subject orientation change in body position and assigning a new body position to the stable end-expiratory value by said processor, and (vi) providing said new body position to a data output interface communicating with varied output devices by said processor.

2. The method of claim 1, further comprising:

(i) substantially continuously determining a first anatomical characteristic representing a first linear displacement of a subject's rib cage in a first orientation, (ii) substantially continuously determining a second anatomical characteristic representing a first linear displacement of a subject's abdomen in a first orientation, and (iii) substantially continuously determining a third anatomical characteristic representing a first axial displacement of a subject's chest wall in a first orientation.

3. The method of claim 2, further comprising storing a first relationship adapted to determine at least a rib cage volume-motion coefficient, an abdomen volume-motion coefficient, and a chest wall volume-motion coefficient, and a second relationship adapted to determine a ventilation characteristic as a function of said first, second, and third anatomical characteristics and said rib cage, abdomen and chest wall volume-motion coefficients.

4. The method of claim 3, wherein said monitoring of said end-expiratory value further comprises applying appropriate volume-motion coefficients associated with said subject orientations during sleep.

5. The method of claim 4, further comprising applying said appropriate volume-motion coefficients to a three degrees of freedom model for non-invasively calculating a tidal volume in said subject orientation during sleep.

6. The method of claim 5, further comprising non-invasively calculating said tidal volume in said subject orientations during wakefulness.

7. The method of claim 1, wherein the axial dimension comprises a distance Xi between a xiphoid and a pubic symphysis for said subject orientation.

8. A pulmonary ventilation system for simultaneously monitoring body position and respiration of a subject, comprising:

(i) means for monitoring a subject orientation, so as to allow monitoring of an end-expiratory value of an axial dimension of a distance Xi between a first location and a second location for said subject orientation, (ii) means for assigning a body position for said end-expiratory value for said subject orientation during a calibration maneuver in which said subject is asked to assume varied body positions, wherein transient voltage spikes are used to signal a change in said subject orientation, (iii) means for determining an end-expiratory value that is stable following said subject orientation change and assigning a new body position to the stable end-expiratory value, and (iv) means for outputting said new body position to a data output interface communicating with varied output devices.

9. The pulmonary ventilation system of claim 8, further comprising:

(i) means for substantially continuously determining a first anatomical characteristic representing a first linear displacement of a subject's rib cage in a first orientation, (ii) means for substantially continuously determining a second anatomical characteristic representing a first linear displacement of a subject's abdomen in a first orientation, and (iii) means for substantially continuously determining a third anatomical characteristic representing a first axial displacement of a subject's chest wall in a first orientation.

10. The pulmonary ventilation system of claim 9, further comprising a storage means adapted to store a first relationship to determine at least a rib cage volume-motion coefficient, an abdomen volume-motion coefficient and a chest wall volume-motion coefficient, and a second relationship adapted to determine a ventilation characteristic as a function of said first, second, and third anatomical characteristics and said rib cage, abdomen and chest wall volume-motion coefficients.

11. The pulmonary ventilation system of claim 10 further comprising means for associating said end-expiratory value with appropriate volume-motion coefficients associated with said subject orientations during sleep.

12. The pulmonary ventilation system of claim 11 further comprising means for applying said appropriate volume-motion coefficients to a three degrees of freedom model to non-invasively calculate a tidal volume in said subject orientation during sleep.

13. The pulmonary ventilation system of claim 12, wherein said tidal volume is non-invasively calculated by said means for applying said appropriate volume-motion coefficients in said subject orientations during wakefulness.

14. The pulmonary ventilation system of claim 8, wherein the axial dimension comprises a distance Xi between a xiphoid and a pubic symphysis for said subject orientation.

* * * * *